US012698407B2

(12) United States Patent
Mörö et al.

(10) Patent No.: US 12,698,407 B2
(45) Date of Patent: Aug. 4, 2026

(54) BIOINK

(71) Applicant: TAMPERE UNIVERSITY FOUNDATION SR, Tampereen Yliopisto (FI)

(72) Inventors: Anni Mörö, Tampereen Yliopisto (FI); Oommen Podiyan Oommen, Tampereen Yliopisto (FI)

(73) Assignee: TAMPERE UNIVERSITY FOUNDATION SR, Tampereen Yliopisto (FI)

( * ) Notice: Subject to any disclaimer, the term of this patent is extended or adjusted under 35 U.S.C. 154(b) by 203 days.

(21) Appl. No.: 18/577,205

(22) PCT Filed: Jun. 10, 2022

(86) PCT No.: PCT/FI2022/050403
§ 371 (c)(1),
(2) Date: Jan. 5, 2024

(87) PCT Pub. No.: WO2023/041836
PCT Pub. Date: Mar. 23, 2023

(65) Prior Publication Data

US 2024/0166900 A1 May 23, 2024

(30) Foreign Application Priority Data

Sep. 15, 2021 (FI) ..................................... 20215971

(51) Int. Cl.

| | |
|---|---|
| ***C09D 11/14*** | (2006.01) |
| ***A61L 27/20*** | (2006.01) |
| ***A61L 27/38*** | (2006.01) |
| ***B33Y 70/00*** | (2020.01) |
| ***C08J 3/24*** | (2006.01) |
| ***C08L 5/08*** | (2006.01) |
| ***C09D 105/08*** | (2006.01) |

(52) U.S. Cl.
CPC .............. *C09D 11/14* (2013.01); *A61L 27/20* (2013.01); *A61L 27/383* (2013.01); *B33Y 70/00* (2014.12); *C08J 3/246* (2013.01); *C08L 5/08* (2013.01); *C09D 105/08* (2013.01); *C08J 2305/08* (2013.01); *C08L 2201/06* (2013.01); *C08L 2205/025* (2013.01)

(58) Field of Classification Search
CPC .............. A61L 27/20; C08J 3/246; C08L 5/08
See application file for complete search history.

(56) References Cited

U.S. PATENT DOCUMENTS

| | | | | |
|---|---|---|---|---|
| 5,213,720 A * | 5/1993 | Civerchia ........ | B29D 11/00038 264/2.6 |
| 2018/0104348 A1 | 4/2018 | Xia et al. | |
| 2020/0101194 A1 | 4/2020 | Kim et al. | |
| 2020/0121713 A1 | 4/2020 | Ranatunga et al. | |

FOREIGN PATENT DOCUMENTS

| | | |
|---|---|---|
| CN | 111303459 B | 2/2021 |
| CN | 110522948 B | 8/2021 |
| WO | 2020127407 A1 | 6/2020 |

OTHER PUBLICATIONS

Koivusalo, L. et al. "Tissue adhesive hyaluronic acid hydrogels for sutureless stem cell delivery and regeneration of corneal epithelium and stroma" Biomaterials 225 (2019) 119516 (Year: 2019).*
Koivusalo et al., "Tissue adhesive hyaluronic acid hydrogels for sutureless stem cell delivery and regeneration of corneal epithelium and stroma", Biomaterials, Elsevier, Amsterdam, NL, vol. 225, Sep. 23, 2019, 13 pages.
International Search Report for PCT/FI2022/050403 mailed Sep. 30, 2022, 4 pages.
Written Opinion of the ISA for PCT/FI2022/050403 mailed Sep. 30, 2022, 6 pages.
International Preliminary Report on Patentability for PCT/FI2022/050403 completed Sep. 11, 2023, 7 pages.
Finland Search Report for FI20215971 dated Apr. 3, 2022, 2 pages.
Shujiang Wang et al., "Mild and Efficient Strategy for Site-selective Aldehyde Modification of Glycosaminoglycans: Tailoring Hydrogels with Tunable Release of Growth Factor", Biomacromolecules, Publication Date: May 30, 2013, 12 pages.

* cited by examiner

*Primary Examiner* — Andrew S Rosenthal
(74) *Attorney, Agent, or Firm* — NIXON & VANDERHYE

(57) ABSTRACT

This relates to a hydrogel precursor composition and to a bioink obtainable from the hydrogel precursor composition, as well as a method of preparing and using the same. More specifically, This also relates to a bioink that contains a catechol grafted and spontaneously crosslinked hydrogel including cells, and to its use in 3D bioprinting and to a method of preparing the same.

7 Claims, 13 Drawing Sheets

A

B

C

A

B

C

BIOINK

CROSS-REFERENCE TO RELATED APPLICATIONS

This application is the U.S. national phase of International Application No. PCT/FI2022/050403 filed Jun. 10, 2022 which designated the U.S. and claims priority to FI 20215971 filed Sep. 15, 2021, the entire contents of each of which are hereby incorporated by reference.

TECHNICAL FIELD

The present invention relates to bioinks and methods of preparing and using the same. More specifically, the invention relates to a bioink that contains a crosslinked hydrogel obtainable from a hydrogel precursor composition, and material of biological origin such as cells. The invention also relates to use of the hydrogel or the bioink in 3D printing and to the method of 3D printing the same.

BACKGROUND 3D bioprinting is a powerful technology for generation of tissue and organ-like structures and it offers great potential to engineer artificial tissues. Bioprinting is a form of additive manufacturing, where 3D living structures are created in a layer-by-layer manner using computer aided designs. 3D bioprinting allows precise spatial placement of cells into patient-specific constructs or implants mimicking complex and irregular shapes of the native tissue. Despite the potential of this emerging technology, there are still technological challenges limiting its wider use in tissue engineering and regenerative medicine.

Bioinks are generally materials that contain a single or multi component matrix components with living cells or growth factors that are loaded into 3D bioprinters to produce native tissue-like constructs. A few requirements have been set for bioinks to perform well in 3D bioprinting. Bioink needs to be printable and hold its 3D shape after printing. These properties need to be combined with structural stability, biocompatibility and effective biological performance. Current bioinks have failed to optimize all of these aspects in a single bioink.

Bioinks can be produced from a variety of materials to answer specific requirements for each application. A hydrogel composition with the ability to be extruded through a small-sized nozzle, and subsequently, to form a shape-stable gel is considered as a suitable base for a bioink, into which living cells can be incorporated. Despite the advancements in hydrogel and bioink development, incorporation of tissue-adhesive components to hydrogels and bioinks is somewhat less investigated. Catechols have been explored in tissue-engineering applications, to increase the tissue adhesive properties of the hydrogels, and many tissue adhesive hydrogels based on catechol chemistry have been introduced so far. However, these hydrogels are mostly formed either through auto-oxidation, self-polymerization, or metal-coordination polymerization, which formation routes can sacrifice cell functionality and, hence, be bioincompatible with cells. Furthermore, many bioinks require photo initiators and photo crosslinking for structural stability of the hydrogel base, which can act as a serious limitation on biological functionality of the bioink.

Click chemistry-based hydrogels are configured to be formed upon mixing the reactive reagents, followed by spontaneous crosslinking of the components. Such hydrogels are shown to be able to encapsulate live cells with a high cell viability. Generally, the click chemistry reactions are fast, spontaneous, versatile and extremely selective, and can result in high yields of products when two molecular substances or components are combined. In this regard, hyaluronic acid (HA) based crosslinked hydrogels have been explored and the crosslinking of these hydrogels occurs rapidly, resulting in a relatively narrow biofabrication window. For example, Koivusalo et al. 2019 discloses a HA-based hydrazone crosslinked hydrogel with an unsuitable gelation rate and viscosity for 3D printing.

Despite existing bioink compositions with tissue adhesive properties, there is still a need for novel bioinks with improved tissue adhesive properties, which are not dependent on self-polymerization, oxidation nor metal coordinated polymerization of the tissue adhesive components. There is also need for novel bioink compositions that provide a suitable crosslinking rate and therefore an optimal biofabrication window for 3D printing. There is also need for novel bioink compositions that allow cell proliferation and tissue differentiation and maturation towards more specialized cellular phenotype. Moreover, there is a need for bioinks that do not use photo initiators and photo crosslinking for enhanced printability and structural stability.

SUMMARY

The present application concerns the inventions defined in the appended independent claims, and their embodiments disclosed below. The appended claims define the scope of protection. Any method, process, product or apparatus disclosed in the description or drawing which is not covered by a claim is provided as an example which is not an embodiment of the claimed invention, but which is useful for understanding the claimed invention.

Herein is described a hydrogel precursor composition, which can be utilized in preparation of a hydrogel and a bioink. The hydrogel and the bioink can be used in additive manufacturing, such as 3D and/or 4D printing.

The inventors have surprisingly found, and shown in the examples below, that crosslinked hydrogels with a specific composition are suitable for additive manufacturing and bioprinting when one or more rheological modifiers are incorporated into the hydrogel composition.

According to a first aspect is provided a hydrogel precursor composition comprising:

- i a first component comprising a hyaluronic acid (HA) component conjugated to
  - a. at least one first reactive functional group, and
  - b. at least one catechol and/or phenol group;
- ii a second component comprising a hyaluronic acid (HA) component conjugated to at least one second reactive functional group; and
- iii at least one rheological modifier component;

wherein the at least one second reactive functional group is configured to form a crosslink with the at least one first reactive functional group.

According to a second aspect is provided a bioink obtainable by mixing the hydrogel precursor composition of the first aspect with a fluid comprising cells.

According to a third aspect is provided use of the hydrogel precursor composition of the first aspect, or the bioink of the second aspect, for additive manufacturing, such as 3D printing.

According to a fourth aspect is provided a method for 3D printing the bioink, the method comprising:

a) mixing the hydrogel precursor composition of the first aspect with a fluid comprising cells;
b) allowing the first component of the hydrogel precursor composition to crosslink with the second component of the hydrogel precursor composition in said fluid, and
c) 3D printing the bioink when the viscosity of the bioink is 200-2000 Pa·s.

According to a further aspect is provided a hydrogel precursor composition comprising: i) a first component comprising a hyaluronic acid (HA) component conjugated to at least one first reactive functional group, and to at least one catechol and/or phenol group; ii) a second component comprising a hyaluronic acid (HA) component conjugated to at least one second reactive functional group; and iii) at least one rheological modifier component with a molecular weight of 1200 kDa-1900 kDa; wherein the at least one second reactive functional group is configured to form a crosslink with the at least one first reactive functional group. According to a further aspect is provided a hydrogel precursor composition comprising: i) a first component comprising a HA component conjugated to at least one carbohydrazide group (—$CONHNH_2$) and to at least one catechol group; ii) a second component comprising a HA component conjugated to at least one aldehyde group (—CHO), and iii) at least one rheological modifier component with a molecular weight of 1200 kDa-1900 kDa. According to a further aspect is provided a hydrogel precursor composition comprising: i) a first component comprising a HA component conjugated to at least one carbohydrazide group (—$CONHNH_2$) and to at least one dopamine group (DA); ii) a second component comprising a HA component conjugated to at least one aldehyde group (—CHO), and iii) at least one rheological modifier component comprising HA with a molecular weight of 1200 kDa-1900 kDa According to a further aspect is provided a hydrogel precursor composition comprising: i) a first component comprising a HA component conjugated to at least one semicarbazide and to at least one catechol group; ii) a second component comprising a HA component conjugated to at least one ketone, and iii) at least one rheological modifier component with a molecular weight of 1200 kDa-1900 kDa. According to a further aspect is provided a hydrogel precursor composition comprising: i) a first component comprising a HA component conjugated to at least one semicarbazide and to at least one catechol group; ii) a second component comprising a HA component conjugated to at least one aldehyde, and iii) at least one rheological modifier component with a molecular weight of 1200 kDa-1900 kDa. According to a further aspect is provided a hydrogel precursor composition comprising: i) a first component comprising a HA component conjugated to at least one aminooxy and to at least one catechol group; ii) a second component comprising a HA component conjugated to at least one ketone, and iii) at least one rheological modifier component with a molecular weight of 1200 kDa-1900 kDa. According to a further aspect is provided a hydrogel precursor composition comprising: i) a first component comprising a HA component conjugated to at least one aminooxy and to at least one catechol group; ii) a second component comprising a HA component conjugated to at least one aldehyde, and iii) at least one rheological modifier component with a molecular weight of 1200 kDa-1900 kDa. According to a further aspect is provided a hydrogel composition, obtainable by mixing the hydrogel precursor composition of the first aspect with a fluid. According to a further aspect is provided a hydrogel composition, obtainable by spontaneous crosslinking of the components of the hydrogel precursor composition of the first aspect mixed with a fluid. According to a further aspect is provided a hydrogel composition, obtainable by spontaneous hydrazone crosslinking of the first and second component of the hydrogel precursor composition of the first aspect when the said hydrogel precursor composition is mixed with a fluid. According to a further aspect is provided a hydrogel composition obtainable by mixing the hydrogel precursor composition of the first aspect with a fluid, wherein the hydrogel composition can be used in additive manufacturing. According to a further aspect is provided a method for 3D printing a hydrogel composition, the method comprising: a) mixing the hydrogel precursor composition with a fluid; b) allowing the first component of the hydrogel precursor composition to crosslink with the second component of the hydrogel precursor composition in said fluid, and c) 3D printing the hydrogel composition when the viscosity of the hydrogel composition is 200-2000 Pa·s.

In an embodiment, the present invention relates to a hydrogel precursor composition for obtaining a printable hydrogel composition. In an embodiment, the present invention relates to the hydrogel composition for 3D printing. In an embodiment, the present invention relates to a bioink composition for 3D bioprinting, the bioink composition comprising the hydrogel composition mixed with cells. In an embodiment, the present invention relates to a method of 3D printing.

The present hydrogel precursor composition is advantageous in enabling a suitable crosslinking rate between the components of the hydrogel composition allowing an adequate fabrication period for the crosslinked hydrogel to be used in 3D printing. The present hydrogel precursor composition is advantageous in having a high modularity due to modular linker moieties and reactive functional groups, as well as due to modularity in the rheological modifier component consistency.

The present hydrogel composition, obtainable from the present hydrogel precursor composition, is advantageous in having an improved performance in printability and retention of shape after printing. The hydrogel composition obtainable from the present hydrogel precursor composition, is further advantageous in having an improved shear thinning and viscoelastic properties, allowing 3D printing of the hydrogel. The present hydrogel composition, obtainable from the present hydrogel precursor composition, is advantageous in having optimized crosslinking rate, allowing the hydrogel to be used in 3D printing. The present hydrogel composition is advantageous as the spontaneous biorthogonal crosslinking of the hydrogel composition is easy to control, therefore differing from the ionically or photochemically crosslinked hydrogels.

The present bioink is advantageous in having high biocompatibility with cells mixed in it, in allowing proliferation of cells, and in differentiation and maturation of cells towards more specialized cellular phenotype and towards a mature tissue. The present bioink is advantageous in comprising tissue adhesive components assisting in integration of printed structures to host tissue upon transplantation. The present bioink is also advantageous in having an improved shear thinning and viscoelastic properties, optimized crosslinking rate and retention of shape after printing, allowing the bioink to be used in 3D printing. The present bioink is also advantageous in being obtainable through a crosslinking reaction of the hydrogel precursor composition components, which is not harmful for cells. The present bioink is also advantageous in comprising only components which are biodegradable in vivo.

The present use of the hydrogel precursor composition of the first aspect, or the bioink of the second aspect, is advantageous in allowing the use in many applications, and allowing many modifications of the use. For example, the hydrogel precursor composition or the bioink can be used with various printing equipment, or with broad range of 3D/bioprinting techniques. The present use of the hydrogel precursor composition or the bioink is advantageous in being configured to be used as an in situ injectable for repair and regeneration of damaged tissues.

The present method for 3D printing of a hydrogel composition is advantageous in having high modularity in regards of the process conditions. The present method for 3D printing of a hydrogel composition is advantageous in neither being based on ionic crosslinking, nor requiring a specific crosslinking inducer, such as specific temperature or a wavelength of light, as the formation of the crosslinks between the first and second component of the hydrogel precursor composition is configured to be spontaneous.

As shown in the examples provided below, the claimed hydrogel precursor composition, the resulting printable hydrogel composition and the bioink obtained with the hydrogel precursor composition, have an improved performance when used in 3D printing when compared to the products known in the art.

Exemplifying and non-limiting embodiments of the invention, both as to constructions and to methods of operation, together with additional objects and advantages thereof, are best understood from the following description of specific exemplifying embodiments when read in connection with the accompanying figures.

BRIEF DESCRIPTION OF THE FIGURES

Some example embodiments will be described with reference to the accompanying figures, in which.

DETAILED DESCRIPTION

Figure 1:
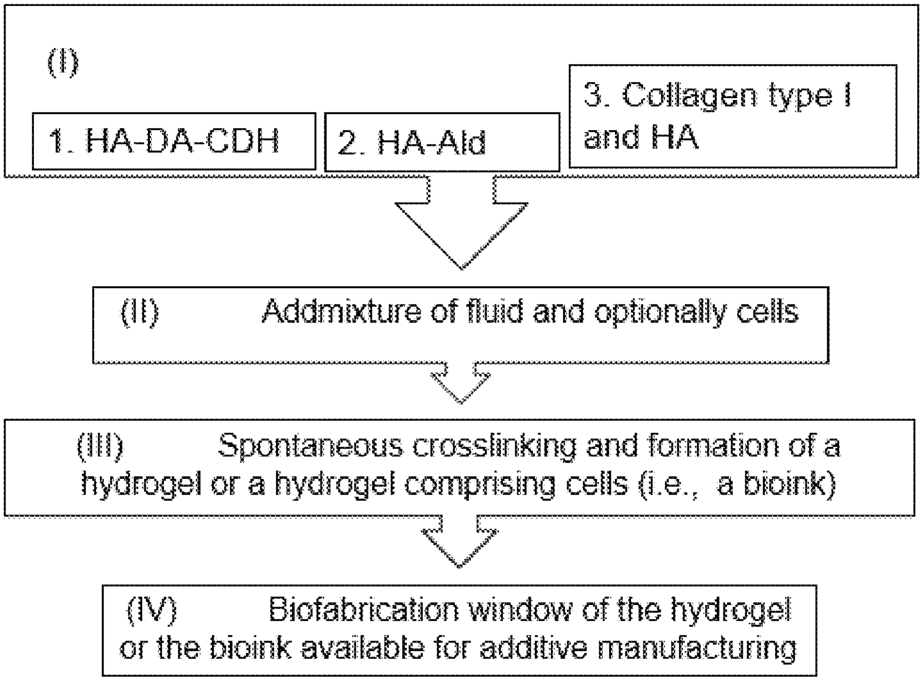
FIG. 1 shows a schematic presentation of the production of an exemplary hydrogel or a bioink according to an example embodiment.

The verbs “comprise”, “contain” and “include” are used in this document as open-ended expressions that neither exclude nor require the existence of un-recited features. As used herein, the term “comprising” includes the broader meanings of “including”, “containing”, and “comprehending”, as well as the narrower expressions “consisting of” and “consisting only of”. The features recited in the accompanied depending claims are mutually freely combinable unless otherwise explicitly stated. Furthermore, it is to be understood that the use of “a” or “an”, i.e. a singular form, throughout this document does not exclude a plurality.

As used herein, the term "additive manufacturing" refers to 3D and 4D printing of material, based on a computer guided digital model. The term 3D additive manufacturing, or 3D printing, can refer to applying material to a surface of an object in a single-layer by printing, or forming a mono-layer coating of, e.g., a hydrogel. The term 3D additive manufacturing or 3D printing can also refer to printing material layer by layer resulting in multilayered, (i.e., >1 printed layers) construction of a three-dimensional object. The term 4D additive manufacturing or 4D printing refers to 3D printing, wherein the 3D printed material is able to morph into different form post-printing. Therefore the term 3D printing comprises also the term 4D printing. The term 3D additive manufacturing or 3D printing can also refer to printing on a surface, such as a substrate, or printing into a support bath including FRESH printing. The term 3D additive manufacturing or 3D printing can also refer to printing of a material comprising material of biological origin, such as living cells. Therefore by the term 3D printing can also be meant the term bioprinting or 3D bioprinting.

As used herein, the term "bioprinting" refers to a method of 3D printing of material, wherein the printed material, such as bioink, comprises material of biological origin, such as living cells.

As used herein, the term "hydrazone crosslinking" means a spontaneous click-type reaction conjugating two biocompatible biomolecules or biopolymers, wherein the crosslinking reaction takes place between an aldehyde group and a hydrazide-group which are grafted to the biomolecules or biopolymers. A crosslink comprising a hydrazone bond comprises a —C(O)—NH—N═C— bond.

As used herein, the term "biofabrication window", in context of the hydrogel or the bioink according to the current invention, refers to the time period during which the cross-linked hydrogel or the bioink has a consistency allowing its use in additive manufacturing.

As used herein, the term "aldehyde group" refers to a functional group comprising or consisting of an aldehyde with the chemical formula —CHO, wherein a carbonyl center is carbon double-bonded to oxygen and single-bonded to hydrogen.

As used herein, the term "catechol group" refers to a functional group comprising or consisting of a catechol, wherein a benzene core carries two hydroxy substituents ortho to each other.

As used herein, the term "carbohydrazide group" refers to a functional group comprising or consisting of a carbohydrazide where the carbonyl group (C═O) is flanked by a hydrazide group (—NH—$NH_2$).

As used herein, the term "carboxylic group" or "carboxyl group" consists of a carbonyl group (C═O) that has a hydroxyl group (O—H) attached to the carbon atom.

As used herein, the term "extracellular matrix protein" refers to any protein found in a large network of proteins, macromolecules and minerals and other molecules that surround, support, and give structure from the outside to cells and tissues in vivo.

As used herein, the term "rheological modifier" refers to a component, which when added to a composition is able to modify the rheological properties of the said composition, such as viscosity, viscoelasticity, torque, shear stress and shear rate.

As used herein, the term "rheological modifier component" means a component configured to improve the rheological properties of the hydrogel composition. A rheological modifier component comprises at least one rheological modifier, for example, two or three rheological modifiers. A rheological modifier component can comprise one or more polymeric or non-polymeric components, which can be, for example, proteins and/or polysaccharides. The rheological modifier component, when added to the hydrogel precursor composition, is at least able to modify the rheological properties of the resulting hydrogel composition, such as viscoelasticity, viscosity, torque, shear stress and shear rate. Optionally, the rheological modifier component can also have other effects when added to a composition, such as increasing the biocompatibility of cells.

As used herein, the term "hyaluronic acid (HA)" means a polymer of disaccharides, which are composed of D-glucuronic acid and N-acetyl-D-glucosamine pairs as repeating units, linked via alternating β-(1→4) and β-(1→3) glycosidic bonds. Hyaluronic acid can be approximately up to 25,000 disaccharide repeats in length. With the term hyaluronic acid may also be meant a salt and/or a solvate of hyaluronic acid, such as sodium hyaluronate. With the abbreviation HA is meant hyaluronic acid. As used herein, the term hyaluronic acid (HA) may be used to refer to HA in the HA component (see below), or HA in the rheological modifier component, for example.

As used herein, the term "disaccharide repeat unit of a HA component" refers to a repeating disaccharide unit of the HA polymer, composed of the said D-glucuronic acid and N-acetyl-D-glucosamine pairs. As used herein, the term "hyaluronic acid (HA) component" means a component of the hydrogel precursor composition comprising hyaluronic acid (HA) or a salt or solvate thereof. In an embodiment, the hyaluronic acid component consists entirely of HA. With the term "HA component" is meant hyaluronic acid component. The HA component can refer to the HA component of the first and/or to the second component of the hydrogel precursor composition.

As used herein, the term "moiety" means a part of a molecule, which can be functionally or structurally identified in the structure of the said molecule. A moiety may be a functional group, or it describes a portion of a molecule with multiple functional groups sharing common structural aspects.

As used herein, the term "fluid" refers to a liquid or gaseous substance. In a hydrogel composition, the fluid is by definition water or an aqueous solution or suspension, such as cell culture medium, buffer solution, saline solution and/or sucrose solution.

As used herein, the term "component" refers to a one individual constituent part, wherein when used in a composition, it forms together with all the other components the entire composition. A component may comprise several different compounds or consist entirely of one specific compound or molecule.

As used herein, the term "viscosity" refers to dynamic viscosity of the fluid, for which measurement unit Pa·s (pascal-second) is used.

As used herein, the term "conjugated" refers to two moieties or compounds being joined together by being directly joined together with another, or by being indirectly joined together through another moiety or compound. Conjugate refers to a compound formed by the conjugation of two or more compounds together.

As used herein, the term "reactive functional group" refers to a functional group or a moiety of a compound which is intended, or may reasonably be expected, to undergo chemical reaction in the experimental set up in question. In an embodiment, the reactive functional group is expected to undergo chemical reaction with a specific reaction partner (which is also a functional group or a moiety) once the said reaction partner is brought in contact with the reactive functional group.

As used herein, the term "crosslink" means a chemical bond or a short sequence of bonds that links one polymer chain or a molecule to another.

As used herein, the term "linker" means a modular region connecting two adjacent moieties within the first or within the second component of the hydrogel precursor composition.

As used herein, the term "biocompatibility" describes the property of a material to be compatible with living cells or tissue and to sustain the viability of the cells, and the ability to not produce any toxic side-effect or immunological response when exposed to the body or bodily fluids.

As used herein, the term "wt-%" signifies weight percentage. The wt-% of a substance in a mixture means the proportion by weight of the substance in the total weight of the mixture. The wt-% is calculated by dividing the weight of the test substance by the weight of the whole mixture.

The hydrogel precursor composition comprises:

i) a first component comprising a hyaluronic acid (HA) component conjugated to
  a) at least one first reactive functional group, and
  b) at least one catechol and/or phenol group;
ii) a second component comprising a hyaluronic acid (HA) component conjugated to at least one second reactive functional group; and
iii) at least one rheological modifier component;

wherein the at least one second reactive functional group is configured to form a crosslink with the at least one first reactive functional group.

Accordingly, it is an object of the present disclosure to provide a hydrogel precursor composition comprising i. a first component comprising a hyaluronic acid (HA) component conjugated to
  a. at least one first reactive functional group, and
  b. at least one catechol and/or phenol group;
ii. a second component comprising a hyaluronic acid (HA) component conjugated to at least one second reactive functional group; and
iii. at least one rheological modifier component;

wherein the at least one second reactive functional group is configured to form a crosslink with the at least one first reactive functional group and wherein the at least one rheological modifier component comprises hyaluronic acid with a molecular weight of 1200 kDa-1900 kDa, and the at least one rheological component comprises 2-50 wt-% from the total weight of the hydrogel precursor composition.

In an embodiment, in the hydrogel precursor composition i) the at least one first reactive functional group is selected from a hydrazide, a hydrazine, a carbohydrazide, an aminooxy, an amine, a semicarbazide, a thiosemicarbazide and/or a carbazate group, preferably the at least one first reactive functional group is carbohydrazide group (—$CONHNH_2$), and the at least one second reactive functional group is an aldehyde group (—CHO), and/or
ii) the at least one first reactive functional group is semicarbazide or aminooxy, and the at least one second reactive functional group is ketone.

In an embodiment, the hydrogel precursor composition comprises:

i) a first component comprising the HA component conjugated to the at least one first reactive functional group and to the at least one catechol group, wherein the at least one first reactive group is a carbohydrazide group (—$CONHNH_2$);
ii) a second component comprising the HA component conjugated to the at least one second reactive functional group, wherein the at least one second reactive functional group is an aldehyde group (—CHO); and
iii) at least one rheological modifier component.

In an embodiment, the HA component of the first component consists entirely of HA polymer. In an embodiment, the HA component of the first component consists of a HA polymer with a molecular weight of 100-1000 kDa, preferably 100-300 kDa.

In an embodiment, the HA component of the second component consists entirely of HA polymer. In an embodiment, the HA component of the second component consists of a HA polymer with a molecular weight of 100-1000 kDa, preferably 100-300 kDa.

In an embodiment, the at least one first reactive functional group of the first component is a carbohydrazide group consisting of a —$CONHNH_2$ moiety.

In an embodiment, the first component comprises at least one catechol group or a derivative thereof. In an embodiment, the first component comprises a catecholamine or a derivative thereof conjugated to the HA component. In a preferable embodiment, the at least one catechol group of the first component comprises or consists of a dopamine group (DA) conjugated to the HA component.

In an embodiment, the hydrogel precursor composition comprising at least one catechol group is configured to generate a non-collapsible hydrogel composition when fluid is added to the hydrogel precursor composition.

In an embodiment, the first component comprises at least one phenol group. In an embodiment, the hydrogel precursor composition comprising phenol group is configured to generate a non-collapsible hydrogel composition when fluid is added to the hydrogel precursor composition.

In an embodiment, the at least one second reactive functional group of the second component is an aldehyde group consisting of a —CHO moiety conjugated to the HA component. In an embodiment, the at least one aldehyde group of the second component comprises a —CHO moiety which is conjugated to the HA component.

In an embodiment, the second component of the hydrogel precursor composition is configured to be spontaneously crosslinkable with the first component of the hydrogel precursor composition. In an embodiment, the second component of the hydrogel precursor composition is configured to be spontaneously hydrazone crosslinkable with the first component of the hydrogel precursor composition. In an embodiment, a hydrogel composition is obtainable by mixing the hydrogel precursor composition with a fluid. In a preferable embodiment, the fluid mixed with the hydrogel precursor composition is liquid. The fluid mixed the hydrogel precursor composition can be, for example, water or an aqueous solution such as cell culture medium, buffer solution, saline solution and/or sucrose solution.

In an embodiment, the second reactive functional group (s) of the second component of the hydrogel precursor composition is configured to form a crosslink with the first reactive functional group(s) of the first component of the hydrogel precursor composition. In an embodiment, the second reactive functional group(s) of the second component is configured to form a crosslink with the first reactive functional group(s) of the first component only after the hydrogel precursor composition is mixed with a fluid. In an embodiment, the formation of the crosslinks is configured to be spontaneous and does not require an inducer, such as specific temperature or a wavelength of light. In an embodiment, the formation of the crosslinks is based on spontaneous click chemistry reaction, such as hydrazone crosslinking of the first and second components of the hydrogel precursor composition together.

In an embodiment, the reactive functional groups of the first and second components of the hydrogel precursor composition are configured to form crosslinks, thereby forming a non-collapsible hydrogel composition. In an embodiment, the at least one first reactive functional group of the first component forming the crosslink with the second component is carbohydrazide group. In an embodiment, the at least one first reactive functional group of the first component forming the crosslink with the second component is selected from a hydrazide, a hydrazine an aminooxy, an amine, a semicarbazide, a thiosemicarbazide and/or a carbazate group.

In an embodiment, the at least one first reactive functional group of the first component has an effect on the rheological properties of the resulting crosslinked hydrogel composition. In an embodiment, the at least one first reactive functional group of the first component, such as a carbohydrazide group, is configured to form a strong crosslink with a reactive functional group of the second component.

In an embodiment, the at least one second reactive functional group of the second component, such as an aldehyde group, is configured to form a strong crosslink with a reactive functional group of the first component. In an embodiment, the at least one second reactive functional group of the second component is reactive with the carbohydrazide group of the first component, or with another functional group of the first component. In an embodiment, the at least one second reactive functional group of the second component forming the crosslink with the first component is an aldehyde (—CHO) group.

In an embodiment, the first and second component of the hydrogel precursor composition are configured to be conjugated by forming a crosslink comprising at least one covalent bond. In certain embodiments, the first and second component of the hydrogel precursor composition are configured to form a crosslink comprising a hydrazone (—C(O)—NH—N═C—), an oxime (—C═N—O—), an imine (—C═N—C—), a semicarbazone (—NH—C(O)—NH—N═C—), a thiosemicarbazone (—NH—C(S)—NH—N═C—), or a carbazone (—O—C(O)—NH—N═C—) bond. The crosslinking rate and stability varies depending on the specific crosslink formed between the first and second component of the hydrogel precursor composition. For example, a first component comprising $—NHNHCONHNH_2$ group conjugated to the HA component produces approximately 15 times stronger crosslink with a reactive functional group aldehyde of a second component, than a first component comprising $—NHNHCO(CH_2)_4CONHNH_2$ group conjugated the HA component.

The first or second reactive functional group(s) of the first and the second component, that has the lowest conjugation percentage to HA in the respective component of the hydrogel precursor composition, determines the degree of crosslinking in the hydrogel. In an embodiment, the lowest conjugation percentage of HA with either the aldehyde groups as the second reactive functional groups, or the carbohydrazide groups as the first reactive functional groups, determine the degree of crosslinking in the hydrogel. Nevertheless, if the hydrogel precursor composition comprises one of the reactive functional groups, for example aldehyde or carbohydrazide, in excess, the stability of the hydrogel matrix is increased without having any effect on the degree of crosslinking. This is due to the dynamic nature of the covalent bonds created in the hydrazone crosslinking process, wherein the crosslinks form and break repeatedly and the crosslinking partners can find each other quickly when one of the partners is in excess. The excess of aldehyde groups in the second component increases the tissue adhesive properties of the hydrogel composition.

In an embodiment, the rheological modifier component of the hydrogel precursor composition is configured to modify the rheology of the hydrogel composition obtainable from the crosslinked hydrogel precursor composition. In an embodiment, the rheological modifier component of the hydrogel precursor composition is configured to modify at least the viscoelasticity viscosity, torque, shear stress and shear rate of the hydrogel composition obtainable from the crosslinked hydrogel precursor composition.

In an embodiment, the rheological modifier component of the hydrogel precursor composition is selected from a polysaccharide, a protein, a synthetic polymer or a combination thereof.

In an embodiment, the rheological modifier component of the hydrogel precursor composition is selected from hyaluronic acid, alginate, chitosan, nanocellulose, polyethylene glycol, poloxamer, polyvinyl alcohol, extracellular matrix (ECM) protein, albumin, or mixtures thereof.

In an embodiment, the rheological modifier component of the hydrogel precursor composition comprises an extracellular matrix (ECM) protein selected from gelatin, collagen type I, collagen type III, collagen type IV, collagen type V, laminin, fibronectin, vitronectin, and fragments and/or mixtures thereof.

In an embodiment, the wt-% of the rheological modifier component in the hydrogel precursor composition is dependent on the molecular weight of the rheological modifier component. In an embodiment, the applied wt-% of the rheological modifier component in the hydrogel precursor composition decreases substantially linearly with the increase of the molecular weight of the applied rheological modifier component. The rheological modifier component is configured to modify the rheology and viscosity of the hydrogel obtainable from the crosslinked hydrogel precursor composition, and therefore too high concentration of high molecular weight rheological modifier component results in a hydrogel composition with unnecessarily high viscosity. Similarly, too low concentration of low molecular weight rheological modifier component results in a hydrogel composition with unnecessarily low viscosity.

In an embodiment, The rheological modifier component of the hydrogel precursor composition comprises hyaluronic acid with a molecular weight of 50 kDa-1900 kDa, preferably 500 kDa-1900 kDa, more preferably 1200 kDa-1900 kDa. In an embodiment, the hydrogel precursor composition comprises 2-50 wt-%, preferably 5-40 wt-%, more preferably 7-17 wt-%. of HA as a rheological modifier from the total weight of the hydrogel precursor composition.

In an embodiment, the rheological modifier component of the hydrogel precursor composition consists of HA with a molecular weight of 50 kDa-1900 kDa, preferably 500 kDa-1900 kDa, more preferably 1200 kDa-1900 kDa. In an embodiment, the rheological modifier component consists of HA, and the wt-% of the rheological modifier component from the total weight of the hydrogel precursor composition is 2-50 wt-%, preferably 5-40 wt-%, more preferably 7-17 wt-%. In an embodiment, the rheological modifier component of the hydrogel precursor composition consists of HA with a molecular weight of 1200 kDa-1900 kDa, and the wt-% of the rheological modifier component from the total weight of the hydrogel precursor composition is 7-17 wt-%. In an embodiment, the molecular weight of the HA of the rheological modifier component is selected based on improved performance in printability and retention of shape of the hydrogel composition after 3D printing. In an embodiment, the rheological modifier component comprising HA with the molecular weight of 1200 kDa-1900 kDa is advantageous for printing performance and retention of shape of the hydrogel composition after 3D printing.

In an embodiment, the rheological modifier component of the hydrogel precursor composition comprises human collagen, preferably type I, with a molecular weight of 250-300 kDa. In an embodiment, the hydrogel precursor composition comprises 0.05-40 wt-%, preferably 2-15 wt-%, more preferably 3-8 wt-% of collagen as a rheological modifier from the total weight of the hydrogel precursor composition.

In an embodiment, the rheological modifier component of the hydrogel precursor composition comprises human fibronectin with a molecular weight of 440-530 kDa. In an embodiment, the hydrogel precursor composition comprises 2-50 wt-%, preferably 5-30 wt-%, more preferably 7-12 wt-% of human fibronectin as a rheological modifier from the total weight of the hydrogel precursor composition.

In an embodiment, the rheological modifier component of the hydrogel precursor composition comprises laminin, preferably human or mouse recombinant laminin, with a molecular weight of 400-900 kDa. In an embodiment, the hydrogel precursor composition comprises 0.2-50 wt-%, preferably 0.2-5 wt-%, more preferably 0.2-2.0 wt-% of laminin as a rheological modifier from the total weight of the hydrogel precursor composition.

In an embodiment, the rheological modifier component of the hydrogel precursor composition comprises human or bovine albumin with a molecular weight of 66-67 kDa. In an embodiment, the hydrogel precursor composition comprises 0.2-60 wt-%, preferably 30-60 wt-%, more preferably 54-58 wt-% of albumin as a rheological modifier from the total weight of the hydrogel precursor composition.

In an embodiment, the rheological modifier component comprises more than one rheological modifier. In an embodiment, the rheological modifier component comprises at least HA and another rheological modifier selected from alginate, chitosan, nanocellulose, polyethylene glycol, poloxamer, polyvinyl alcohol, extracellular matrix (ECM) protein, albumin, or mixtures thereof. In an embodiment, the rheological modifier component comprises at least HA and another rheological modifier selected from ECM protein and/or albumin. In an embodiment, the rheological modifier component comprises HA with a molecular weight of 1200-1900 kDa and another rheological modifier selected from ECM protein and/or albumin. In an embodiment, the rheological modifier component comprises HA, configured to improve printing performance and retention of shape of the hydrogel composition, and an ECM protein as another rheological modifier, configured to improve the biocompatibility of the hydrogel precursor composition.

In an embodiment, the rheological modifier component of the hydrogel precursor composition comprises a mixture of HA and collagen, preferably collagen type I. In an embodiment, the hydrogel precursor composition comprises 2-50 wt-%, preferably 9-40 wt-%, more preferably 11-23 wt-% of the mixture of HA and collagen type I as the rheological modifier component, from the total weight of the hydrogel precursor composition.

In an exemplary embodiment, the hydrogel precursor composition comprises 17.6 wt-% of HA with a molecular weight of 1200-1900 kDa as the rheological modifier component. In another exemplary embodiment, the hydrogel precursor composition comprises 5.4 wt-% of human collagen type I with a molecular weight of 300 kDa, and 11.9 wt-% of HA with a molecular weight of 1200-1900 kDa as the rheological modifier component.

In an embodiment, the at least one first reactive functional group and the catechol group of the first component, and the at least one second reactive functional group of the second component are conjugated to the carboxyl group of the glucuronic acid residue of their respective HA component, or to any functional group of their respective HA component. In an embodiment, the at least one carbohydrazide group and the catechol group of the first component and the at least one aldehyde group of the second component are conjugated to the carboxyl group of the glucuronic acid residue of their respective HA component, or to any functional group of their respective HA component. Preferably, the at least one carbohydrazide group and the catechol group of the first component and the at least one aldehyde group of the second component are conjugated to their respective HA component through a substitution of a hydroxyl group (OH) of a glucuronic acid residue of the HA component, or more preferably conjugated to the carboxyl group of the glucuronic acid residue of their respective HA component. In an embodiment, the at least one carbohydrazide group and the catechol group of the first component, and the at least one aldehyde group of the second component are conjugated to their respective HA component directly, or via linker components.

In an embodiment, the at least one first reactive functional group is conjugated to the HA component in the first component directly without any linker in between. Preferably the at least one first reactive functional group is conjugated to a carboxyl group of the glucuronic acid residue of the HA component, or conjugated to the glucuronic acid residue of the HA component through substitution of an —OH group.

In an embodiment, is disclosed the hydrogel precursor composition wherein, the at least one first reactive functional group is conjugated to the HA component of the first component via a linker $L_1$, wherein said linker $L_1$ is conjugated to a carboxyl group of the HA component, preferably through a substitution of a carboxylate hydroxy group of a glucuronic acid residue of the HA component. In an embodiment, is disclosed the hydrogel precursor composition wherein, the at least one first reactive functional group is conjugated to the HA component of the first component via a linker $L_1$, wherein said linker $L_1$ is conjugated to a carboxyl group of the HA component, preferably through a substitution of a carboxylate hydroxy group of a glucuronic acid residue of the HA component, and wherein the linker $L_1$ is formed of 1-10 moieties, each moiety being independently selected from a group consisting of phenylene ($—C_6H_4—$), oxime (—C═N—O—), imine (—C═N—C—), alkylene ($—CH_2—$), containing 1-12 carbon atoms, ethynydiyl (—C≡C—), ethylenediyl (—C═C—), ether (—O—), thioether (—S—), amide (—CO—NH—, —CO—NR'—, —NH—CO— and —NR'—CO—) wherein R' represents an alkyl group containing less than 5 carbon atoms, carbonyl (—CO—), ester (—COO— and —OCC—), disulfide (—SS—), sulfonamide ($—SO_2—NH—$, $—SO_2—NR'—$), sulfone ($—SO_2—$), phosphate ($—O—PO_2—O—$), diaza (—N═N—), diimine (—NHNH—), secondary amine (—NH—) and tertiary amine.

In an embodiment, is disclosed the hydrogel precursor composition, wherein the first component comprises plurality of first reactive functional groups and wherein the first reactive functional groups, or the linkers $L_1$ conjugated to the first reactive functional groups, are conjugated to 5-20%, preferably 9-15%, more preferably 12-13% of disaccharide repeat units of the HA component of the first component.

In an embodiment, is disclosed the hydrogel precursor composition wherein the at least one first reactive functional group is a carbohydrazide group and the linker $L_1$ is —NHNH—.

In a preferable embodiment, the at least one first reactive functional group is carbohydrazide group and it is conjugated to the HA component via the linker $L_1$ in the first component, wherein the linker $L_1$ is preferably conjugated to the HA component via the carboxyl group of the glucuronic acid residue of the HA component. Alternatively, the linker $L_1$ is conjugated to another functional group comprised by the disaccharide repeat units of the HA component.

In an embodiment, the at least one carbohydrazide group is conjugated to a carboxyl group of a glucuronic acid residue of the HA via the linker $L_1$ according to formula (I), wherein n is preferably 250-2500, more preferably n is 250-750.

(I)

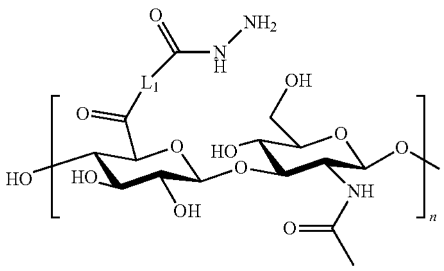

In an embodiment, the at least one carbohydrazide group is conjugated to a glucuronic acid residue of the HA component via the linker $L_1$ through substitution of an —OH group of the glucuronic acid residue. In an embodiment, the —OH group of the glucuronic acid residue is substituted with a linker $L_1$ comprising an α-substituent, such as an amino group or a further hydrazide group.

In an embodiment, the linker $L_1$ of the first component of the hydrogel precursor composition is preferably selected from —NHNH—, and $—NHNH(CH_2)_n—$, wherein n is 1-12, preferably n is 4. In a preferable embodiment, the linker $L_1$ is —NHNH— wherein the linker $L_1$ is conjugated to the HA component via the carboxyl group of the glucuronic acid residue of the HA component.

In an embodiment, the hydrogel precursor composition comprising —NHNH— as the linker $L_1$ in the first component, is configured to form crosslink faster when compared to a hydrogel precursor composition with $—NHNH(CH_2)_n—$ as the linker $L_1$, wherein n is 1-12. In an embodiment, the hydrogel precursor composition comprising —NHNH— as the linker $L_1$, is configured to form a printable hydrogel composition faster, and the formed hydrogel composition is more stable, when compared to a hydrogel precursor composition with a linker $—NHNH(CH_2)_4—$ adipic acid dihydrazide based linkers containing 4 carbons. In an embodiment, the hydrogel precursor composition comprising —NHNH— as the linker $L_1$ in the first component, is configured to form a printable hydrogel composition with increased stability, when compared to a hydrogel precursor composition comprising of $—NHNH(CH_2)_4$ as the linker $L_1$.

In an embodiment, the structure and length of the linker $L_1$ of the first component is optimized for conjugation of the carbohydrazide group with the HA component. The optimal structure and length of the linker $L_1$ allows the carbohydrazide group and the HA component of the first component, to obtain an optimal configuration, enabling an efficient crosslinking of the first component to the second component. Accordingly, the modular structure and length of the linker $L_1$ of the first component facilitates a high stability of the crosslinked hydrogel composition with faster reaction kinetics.

In an embodiment, the first component comprises plurality of first reactive functional groups which are carbohydrazide groups, and the carbohydrazide groups or the linkers $L_1$ conjugated to the carbohydrazide groups, are conjugated to 5-20%, preferably 9-15%, more preferably 12-13% of the disaccharide repeat units of the HA component of the first component. In an embodiment, the said conjugation percentages of the carbohydrazide groups (or the linkers $L_1$) with the disaccharide repeat units of the HA component of the first component, are beneficial for the printability of the hydrogel composition. In an embodiment, wherein the carbohydrazide groups, or the linkers $L_1$ conjugated to the carbohydrazide groups, are conjugated to more than 20% of the disaccharide repeat units of the HA component of the first component, the crosslinking and stability of the hydrogel is improved, but the printability is reduced.

In an embodiment, the at least one phenol and/or catechol group is conjugated to the HA component in the first component directly without any linker in between. Preferably the at least one phenol and/or catechol group is conjugated to a carboxyl group of the glucuronic acid residue of the HA component, or conjugated to the glucuronic acid residue of the HA component through substitution of an —OH group.

In an embodiment, is disclosed the hydrogel precursor composition, wherein the at least one phenol and/or catechol group is conjugated to the HA component of the first component via a linker $L_2$, wherein said linker $L_2$ is conjugated to a carboxyl group of the HA component, preferably through a substitution of a carboxylate hydroxy group of a glucuronic acid residue of the HA component. In an embodiment, is disclosed the hydrogel precursor composition, wherein the at least one phenol and/or catechol group is conjugated to the HA component of the first component via a linker $L_2$, wherein said linker $L_2$ is conjugated to a carboxyl group of the HA component, preferably through a substitution of a carboxylate hydroxy group of a glucuronic acid residue of the HA component, and wherein the linker $L_2$ is formed of 1-10 moieties, each moiety being independently selected from a group consisting of phenylene ($—C_6H_4—$), oxime (—C═N—O—), imine (—C═N—C—), alkylene ($—CH_2—$) containing 1-12 carbon atoms, ethynydiyl (—C≡C—), ethylenediyl (—C═C—), ether (—O—), thioether (—S—), amide (—CO—NH—, —CO—NR'—, —NH—CO— and —NR'—CO—) wherein R' represents an alkyl group containing less than 5 carbon atoms, carbonyl (—CO—), ester (—COO— and —OCC—), disulfide (—SS—), sulfonamide ($—SO_2—NH—$, $—SO_2—NR'—$), sulfone ($—SO_2—$), phosphate ($—O—PO_2—O—$), diaza (—N═N—), diimine (—NHNH—), secondary amine (—NH—), and tertiary amine, preferably the linker $L_2$ is $—NH(CH_2)_2—$.

In an embodiment, is disclosed the hydrogel precursor composition, wherein the first component comprises plurality of catechol groups and/or phenol groups and wherein the catechol and/or phenol groups, or the linkers $L_2$ conjugated to the catechol and/or phenol groups, are conjugated to 1-20%, preferably 2-10%, more preferably 3-6%, even more preferably 3.0-3.6% of disaccharide repeat units of the HA component of the first component.

In an embodiment, the first component of the hydrogel precursor composition comprises at least one catechol group, which is conjugated to the HA component via a linker $L_2$ in the first component, wherein the linker $L_2$ is preferably conjugated to the HA component via the carboxyl group of the glucuronic acid residue of the HA component. Alternatively, the linker $L_2$ is conjugated to another functional group comprised by the disaccharide repeat units of the HA component.

In an embodiment, the at least one catechol group is conjugated to a carboxyl group of a glucuronic acid residue of the HA component via the linker $L_2$ according to formula (II), wherein n is preferably 250-2500, more preferably n is 250-750.

(II)

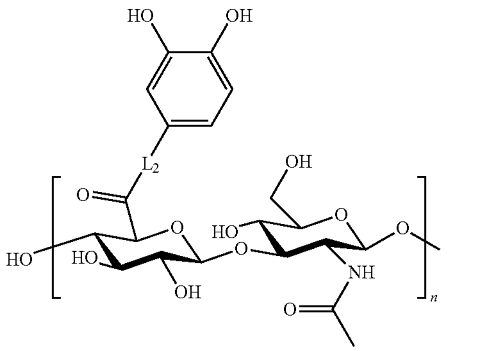

In an embodiment, the at least one catechol group is conjugated to a carboxyl group of a glucuronic acid residue of the HA component via the linker $L_2$ through substitution of an —OH group of the glucuronic acid residue. In an embodiment, the OH group of the glucuronic acid residue is substituted with a linker $L_2$ comprising an α-substituent, such as an amino group.

In an embodiment, the linker $L_2$ of the first component of the hydrogel precursor composition is most preferably $—NH(CH_2)_2—$, wherein the linker $L_2$ is preferably conjugated to the HA component via the carboxyl group of the glucuronic acid residue of the HA component. In a preferable embodiment, the linker $L_2$ is $—NH(CH_2)_2—$.

In an embodiment, the first component comprises plurality of catechol groups, and the catechol groups or the linkers $L_2$ conjugated to the catechol groups, are conjugated to 1-20%, preferably 2-10%, more preferably 3-6%, even more preferably 3.0-3.6% of disaccharide repeat units of the HA component of the first component. The said linkers $L_2$ are preferably conjugated to the carboxyl group of the glucuronic acid units of the HA component of the first component. In an embodiment, the percentage of catechol groups conjugated to the disaccharide repeat units of the HA component of the first component is advantageous to the tissue-adhesive properties, as well as viscoelasticity and shear thinning properties of the final hydrogel composition.

In an embodiment, the hydrogel precursor composition comprising $—NH(CH_2)_2—$ as the linker $L_2$ and a catechol group conjugated to the first component, is configured to form a printable hydrogel composition faster, when compared to a hydrogel precursor composition comprising no catechol group.

In an embodiment, the at least one catechol group is conjugated to the HA component by allowing the amino group of dopamine to react with a carboxyl group of the HA component.

In an embodiment, the at least one second reactive functional group is conjugated to the HA component in the second component directly without any linker in between. Preferably the at least one second reactive functional group is conjugated to a carboxyl group of the glucuronic acid residue of the HA component, or conjugated to the glucuronic acid residue of the HA component through substitution of an —OH group.

In an embodiment, is disclosed the hydrogel precursor composition, wherein the at least one second reactive functional group is conjugated to the HA component of the second component via a linker $L_3$, wherein said linker $L_3$ is conjugated to a carboxyl group of the HA component, preferably through a substitution of carboxylate hydroxy group of a glucuronic acid residue of the HA component. In an embodiment, is disclosed the hydrogel precursor composition, wherein the at least one second reactive functional group is conjugated to the HA component of the second component via a linker $L_3$, wherein said linker $L_3$ is conjugated to a carboxyl group of the HA component, preferably through a substitution of carboxylate hydroxy group of a glucuronic acid residue of the HA component, and wherein the linker $L_3$ is formed of 1-10 moieties, each moiety being independently selected from the group consisting of phenylene ($—C_6H_4—$), oxime (—C═N—O—), imine (—C≡N—C—), alkylene ($—CH_2—$) containing 1-12 carbon atoms, ethynydiyl (—C≡C—), ethylenediyl (—C═C—), ether (—O—), thioether (—S—), amide (—CO—NH—, —CO—NR'—, —NH—CO— and —NR'—CO—) wherein R' represents an alkyl group containing less than 5 carbon atoms, carbonyl (—CO—), ester (—COO— and —OCC—), disulfide (—SS—), sulfonamide ($—SO_2—NH—$, $—SO_2—NR'—$), sulfone ($—SO_2—$), phosphate ($—O—PO_2—O—$), diaza (—N═N—), diimine (—NHNH—), and tertiary amine.

In an embodiment, the second component of the hydrogel precursor composition comprises plurality of second reactive functional groups, preferably aldehyde groups, wherein the second reactive functional groups or the linkers $L_3$ conjugated to the second reactive functional groups, are conjugated to are conjugated to 5-50%, preferably 9-15%, more preferably 11-13% of the disaccharide repeat units of the HA component of the second component.

In an embodiment, the at least one second reactive functional group of the hydrogel precursor composition is an aldehyde group (—CHO) and the linker $L_3$ is $—NHCH_2—$.

In a preferable embodiment, the at least one second reactive functional group is an aldehyde group, which is conjugated to the HA component via a linker $L_3$ in the second component, wherein the linker $L_3$ is preferably conjugated to the HA component via the carboxyl group of the glucuronic acid residue of the HA. Alternatively, the linker $L_3$ is conjugated to another functional group comprised by the disaccharide repeat units of the HA component.

In an embodiment, the at least one second reactive functional group is an aldehyde group, which is conjugated to a carboxyl group of a glucuronic acid residue of the HA component via the linker $L_3$ according to formula (III), wherein n is preferably 250-2500, more preferably n is 250-750.

(III)

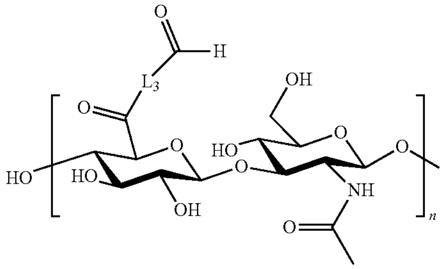

In an embodiment, the at least one aldehyde group is conjugated to a carboxyl group of a glucuronic acid residue of the HA component via the linker $L_3$ through substitution of an —OH group of the glucuronic acid residue. In an embodiment, the —OH group of the glucuronic acid residue is substituted with the linker $L_3$ comprising an α-substituent, such as an amino group.

In an embodiment, the linker $L_3$ of the second component of the hydrogel precursor composition is most preferably $—NH(CH_2)_n—$, wherein n is 1-12, preferably n is 2, more preferably n is 1. In an embodiment, the linker $L_3$ of the second component of the hydrogel precursor composition is most preferably $—NHCH_2—$, wherein the linker $L_3$ is conjugated to the HA component via the carboxyl group of the glucuronic acid residue of the HA component. In an alternative embodiment, the linker $L_3$ of the second component of the hydrogel precursor composition is —NHNH—.

In an embodiment, the structure and length of the linker $L_3$ of the second component is optimized for conjugation of the second reactive functional group with the HA component. The optimal structure and length of the linker $L_3$ allows the aldehyde group and the HA component of the second component, to obtain an optimal configuration, enabling an efficient crosslinking of the first component to the second component. Accordingly, the modular structure and length of the linker $L_3$ of the second component facilitates a high stability of the crosslinked hydrogel composition.

In an embodiment, the aldehyde groups are generated by $NaIO_4$ mediated oxidation of the C2 and C3 hydroxyls in the glucuronic acid residues of the HA component without the use of linker $L_3$ to 5-50%, preferably to 9-15%, more preferably to 11-13% of the disaccharide repeat units of the HA component of the second component. The aldehyde groups generated in this manner by grafting of aminoglycerol groups followed by $NaIO_4$ oxidation is preferred over traditional backbone oxidation to minimize the fragmentation of the polymer and to preserve the bioactivity of the HA. The said approach to generate aldehyde groups by grafting of aminoglycerol groups followed by $NaIO_4$ oxidation provides an improved control over the degree of aldehyde groups conjugated to the disaccharide repeat units of the HA component of the second component.

In a preferable embodiment, the carbohydrazide groups or the linkers $L_1$ conjugated to the carbohydrazide groups, are conjugated to 12-13% of the disaccharide repeat units of the HA component, and the catechol groups or the linkers $L_2$ conjugated to the catechol groups, are conjugated to 3.0-3.6% of the disaccharide repeat units of the HA component in the first component. In a preferable embodiment, the aldehyde groups or the linkers $L_3$ conjugated to the aldehyde groups are conjugated to 11-13% of the disaccharide repeat units of the HA component of the second component.

In an embodiment, the hydrogel precursor composition comprises also at least one regulatory signal component, selected from growth factors, antibodies, hormones, peptides, polypeptides, nanoparticles, and fragments and/or mixtures thereof. In an embodiment, the regulatory signal component comprises heparin, heparin derived nanoparticle, growth factor encapsulated nanocarrier, and/or growth factor immobilized biomaterial adapted to stabilize growth factor(s). In an embodiment, the regulatory signal component comprises a nanoparticle which is a super paramagnetic iron oxide NPs (SPIONs). In an embodiment, the regulatory signal component comprises a gold nanoparticle that imparts conductive characteristics when utilizing neurons, cardiomyocytes or myoblast cells in the bioink. The at least one regulatory signal component of the hydrogel precursor composition is selected based on the cell type mixed with the hydrogel precursor composition, for obtaining printable bioink. In an embodiment, the at least one regulatory signal component mixed with the hydrogel precursor composition is configured to induce or promote differentiation of the cells mixed in the hydrogel precursor composition. In an embodiment, the at least one regulatory signal component mixed with the hydrogel precursor composition is configured to promote cell proliferation, adhesion, cell fate determination, and/or affect the secretome of the cells mixed in the hydrogel precursor composition. In an embodiment, the at least one regulatory signal component mixed with the hydrogel precursor composition is configured to promote tissue architecture development of the cells mixed in the hydrogel precursor composition.

According to a preferable embodiment the at least one rheological modifier component of the hydrogel precursor component according comprises hyaluronic acid with a molecular weight of 1200 kDa-1900 kDa, and collagen, preferably type I with molecular weight of 250-300 wherein and the at least one rheological component comprises 2-50 wt-% preferably 9-40 wt-%, more preferably 11-23 wt-% from the total weight of the hydrogel precursor composition.

The at least one rheological modifier component may comprise also one or more further extracellular matrix proteins preferably selected from gelatin, laminin. fibronectin, vitronectin, and fragments and/or mixtures thereof.

According to a preferable embodiment the at least one first reactive group of the hydrogel precursor component is carbohydrazide and the at least one second reactive group is aldehyde.

According to another preferable embodiment the at least one first reactive group of the hydrogel precursor component is aldehyde and the at least one second reactive group is carbohydrazide.

According to a preferable embodiment molecular weight of the first and the second component is 100-1000 kDa, preferably 100-300 kDa.

In an embodiment, is provided a bioink obtainable by mixing the hydrogel precursor composition with a fluid comprising cells.

In an embodiment, the hydrogel precursor composition and the cells are mixed in a fluid which is isotonic with the cells mixed in it. In an embodiment, the selected fluid creates an isotonic hydrogel composition with the cells mixed in it. In a preferable embodiment, the fluid mixed with cells and the hydrogel precursor composition is liquid. The fluid mixed with cells and the hydrogel precursor composition can be an aqueous solution such as cell culture medium, saline solution such as phosphate buffered saline (PBS), another buffer solution, and/or sucrose solution.

In an embodiment, the cells comprise undifferentiated stem cells, and/or differentiated cells. In an embodiment, the cells comprise human cells, or mammalian cells. In an embodiment, the cells comprise proliferative cells and/or non-proliferative cells. In an embodiment, the cells comprise a mixture of different cell types, preferably of the same species of origin. In an embodiment, the cells comprise hASCs, hASC derived corneal stromal like cells, human pluripotent stem cell (hPSC) derived neuronal cells (NCs) and/or hPSC derived corneal endothelial cells. In an embodiment, the cells comprise hepatocytes, vascular endothelial cells, lymphatic endothelial cells and/or fibroblasts.

In an embodiment, the hydrogel precursor composition and/or the bioink comprise nutrients promoting cell viability in the bioink, the nutrients being selected from amino acids, proteins, peptides, fatty acids, lipids, trace elements, antibiotics, vitamins, inorganic salts, carbohydrates, and/or serum.

In an embodiment, is provided use of the hydrogel precursor composition or the bioink for additive manufacturing, such as 3D printing.

In an embodiment, is disclosed a method for 3D printing the bioink, the method comprising: a) mixing the hydrogel precursor composition with a fluid comprising cells; b) allowing the first component of the hydrogel precursor composition to crosslink with the second component of the hydrogel precursor composition in said fluid, and c) 3D printing the bioink when the viscosity of the bioink is 200-2000 Pa·s.

In an embodiment, the method for 3D printing comprises mixing the hydrogel precursor composition to a fluid comprising cells, thereby obtaining the bioprintable bioink. In an embodiment, the hydrogel is obtainable by spontaneous crosslinking of the components of the hydrogel precursor composition. In an embodiment, the bioink is obtainable by spontaneous crosslinking of the components of the hydrogel precursor composition when the composition is mixed in a fluid comprising cells. The hydrogel precursor composition mixed with fluid is configured to form crosslinks between a reactive functional group of the first component and a reactive functional group of the second component of the hydrogel precursor composition. The resulting crosslinked hydrogel composition is printable with 3D printing methods. The bioink comprising crosslinked hydrogel composition and cells is printable with 3D printing methods.

In an embodiment, the time period during which the crosslinked bioink is printable is limited, wherein the biofabrication window is determined by the composition of the hydrogel precursor composition, and thereby the crosslink formation dynamics of the bioink. The crosslinking of the hydrogel and/or bioink is a continuous process, which starts when the fluid is added to the hydrogel precursor composition. The hydrogel and/or bioink is printable due to adequate amount of crosslinks formed, thereby giving the hydrogel and/or bioink optimal viscosity and shear thinning properties for printing. In an embodiment, stabilizing the printed hydrogel and/or bioink structure, for example by curing, promotes further crosslinking and enhances the stability of the printed bioink structures post-printing.

An exemplary process for obtaining the hydrogel and/or the bioink is shown in FIG. 1. The exemplary hydrogel precursor composition comprises a first component 1. HA-DA-CDH (hyaluronic acid-dopamine-carbohydrazide), a second component 2. HA-Ald (hyaluronic acid-aldehyde) and a third component 3. comprising two rheological modifier components Collagen type I and HA (step (I)). When the hydrogel precursor composition is admixed with a fluid (step (II)), such as buffer or cell culture medium, a spontaneous hydrazone crosslinking reaction occurs together with strong secondary interactions with dopamine and collagen, forming a dual network structure and thereby the hydrogel composition (step (III)). As also indicated in the FIG. 1, the bioink is obtained by mixing the hydrogel precursor composition with a fluid comprising cells. Mammalian cells, such as human adipocyte tissue derived stem cells (hASCs) and hASC derived corneal stromal like cells, are mixed with the hydrogel prior to crosslinking, resulting in the formation of the bioink. The resulting hydrogel and/or a bioink is then suitable for a pre-determined time period (biofabrication window) for additive manufacturing. The bioink can be 3D bioprinted within the biofabrication window, resulting in a viable bioprinted scaffold.

The hydrogel and the bioink comprising the hydrogel must be printable but also adequately stable. The stability is affected by the degree of crosslinking of the hydrogel, which is partially affected by the concentration of the first and second component of the hydrogel precursor composition used in the hydrogel. In an embodiment, the combined concentration of the first component and the second component of the hydrogel precursor composition in the hydrogel composition is preferably 2.5-15.5 mg/ml. In an embodiment, the combined concentration of the first component and the second component of the hydrogel precursor composition in the bioink is preferably 2.5-15.5 mg/ml. The degree of crosslinking of the hydrogel is also affected by the available reactive functional groups of the first and second component of the hydrogel precursor composition. The degree of crosslinking is determined by the limiting amount of the first reactive functional groups in the first component, or the second reactive functional groups in the second component, bound to the disaccharide repeat units of the respective HA component, which amount ever is lower. The degree of crosslinking refers to the percentage of the disaccharide repeat units of the first and second HA components, being conjugated to first reactive functional groups or to second reactive functional groups, which are crosslinked with second reactive functional groups or first reactive functional groups, respectively. The degree of crosslinking of the bioink is potentially further affected by the composition of the linkers $L_1$, $L_2$ and/or $L_3$ of the first and second component of the hydrogel precursor composition. The degree of hydrazone crosslinking formed between the first component and the second component should be below 15% of the total amount of the disaccharide repeat units of the first and second HA components. If the degree of hydrazone crosslinking is more than 15% of the combined amount of disaccharide repeat units of the HA components of the first and second component, the crosslinking occurs too fast, thereby limiting the printability of the hydrogel.

In an embodiment, the crosslinked hydrogel composition and/or the bioink is printable when the viscosity of the hydrogel composition is 100-5000 Pa·s, preferably 200-2000 Pa·s. In an embodiment, the method for 3D printing comprises allowing the first component and the second component of the hydrogel precursor composition to crosslink until viscosity of the admixture reaches 100-5000 Pa·s, preferably 200-2000 Pa·s. In an embodiment, the method for 3D printing comprises 3D printing the hydrogel composition when the viscosity of the hydrogel composition is 100-5000 Pa·s, preferably 200-2000 Pa·s.

In an embodiment, the first component and the second component of the hydrogel precursor composition are configured to crosslink at a temperature of 1-38° C. In an embodiment, the hydrogel crosslinking temperature is a room temperature within the range 18-24° C., preferably 19-22° C. In an embodiment, the optimal temperature for crosslinking of the hydrogel and/or bioink is 1-38° C., preferably 18-24° C. In an embodiment, the optimal temperature for crosslinking of the hydrogel and/or bioink is 1-38° C., preferably 18-24° C., more preferably 19-22° C.

In a preferable embodiment, the crosslinking of the hydrogel and/or bioink is allowed to proceed until viscosity of the hydrogel and/or bioink reaches about 200 Pa·s after which the hydrogel and/or bioink can be used in printing. In an embodiment, the crosslinking of the hydrogel and/or bioink proceeds up to 60 min, preferably for 45-60 min, at 20° C. until viscosity of the hydrogel and/or bioink reaches 200 Pa·s.

In an embodiment, the time period during which the hydrogel and/or bioink is printable, i.e., can be fabricated, is dependent on the used concentration of the crosslinking components, i.e., the first and the second component of the hydrogel precursor composition. In an embodiment, for a hydrogel/bioink comprising 5.83 mg/ml of crosslinking components, the biofabrication window is at least 150 min, or preferably at least 90 min. In an embodiment, the printing pressure for printing the hydrogel/bioink depends on the size of the printing nozzle used.

In an embodiment, the 3D printed hydrogel composition is preferably allowed to form further crosslinks post-printing, to achieve sufficient stability after printing. In an embodiment, the bioink is allowed to stabilize and form further crosslinks after 3D printing, prior to submerging the 3D printed bioinks in isotonic fluid for further processing. In an embodiment, the 3D printed hydrogel composition and/or the bioink is preferably cured for a period of time, prior to submerging the printed hydrogel in isotonic fluid for further processing, to achieve sufficient stability of the hydrogel after printing. In an embodiment, the 3D printed hydrogel composition and/or the bioink is cured for 15-60 min.

EXAMPLES

Example 1. Synthesis of a Dopamine Modified Hyaluronic Acid, as Part of the First Component of the Present Hydrogel Precursor Composition 1 mmol of HA (400 mg, 1 equivalent) was dissolved in 60 mL deionized water, to which 1 mmol HOBt (153 mg, 1 equivalent) and 1 mmol dopamine (190 mg, 1 equivalent) was then added. The pH of the reaction solution was adjusted to 5.5 with 1 M HCl and 1 M NaOH. Then 0.25 mmol EDC (48 mg, 0.25 equivalent) was added in 2 batches at 30 min interval. pH of the solution was maintained at 5.5 for 6 h, and then allowed to stir overnight. The reaction mixture was loaded into a dialysis bag and dialyzed against dilute HCl (pH=3.5) containing 100 mM NaCl (4×2 L, 24 h) followed by dialysis in dilute HCl (pH 3.5, 2×2 L, 24 h) and then dialyzed against deionized water (2×2 L, 24 h). Thereafter, the solution was lyophilized. Since dopamine is conjugated to the carboxyl groups of HA component via it's α-amino group, the linker $L_2$, is —$NH(CH_2)_2$—. Degree of dopamine conjugation was 3.6% (with respect to the disaccharide units of HA) as estimated by NMR

Example 2. Synthesis of Dopamine and Carbohydrazide Modified Hyaluronic Acid (HA-DA-CDH), as the First Component of the Present Hydrogel Precursor Composition The first component comprising a hyaluronic acid (HA) component conjugated to carbohydrazide groups (—$CONHNH_2$) as the first reactive groups, and to catechol groups was synthesized. The conjugation of carbohydrazide (CDH) on dopamine-modified hyaluronic acid (HA-DA) was carried out by carbodiimide coupling chemistry. Briefly, 0.5 mmol of HA-DA (200 mg, 1 equivalent) was dissolved in 120 mL of deionized water. Thereafter, 0.375 mmol carbodihydrazide (34 mg, 0.75 equivalent) and 0.5 mmol HOBt (76.5 mg, 1 equivalent) was added to the aqueous HA-DA solution. The pH of the reaction mixture was adjusted to 4.7. Finally, 0.1 mmol EDC·HCl (20 mg, 0.2 equivalent) was added and allowed to stir overnight. The reaction mixture was loaded into a dialysis bag and dialyzed against dilute HCl (pH=3.5) containing 100 mM NaCl (4×2 L, 24 h) followed by dialysis in dilute HCl (pH 3.5, 2×2 L, 24 h) and then dialyzed against deionized water (2×2 L, 24 h). Thereafter, the mixture was lyophilized to obtain HA-DA-CDH. The degree of hydrazide modifications was found to be 13.2% (with respect to the disaccharide repeat units of HA) as determined using TNBS assay. Since carbodihydrazide ($NH_2NHCONHNH_2$) was allowed to react with the COOH group of the HA-DA, the linker $L_1$ formed is —NHNH—.

Example 3. Synthesis of Aldehyde Modified Hyaluronic Acid (HA-Ald), as the Second Component of the Present Hydrogel Precursor Composition The second component comprising a hyaluronic acid (HA) component conjugated to aldehyde groups (—CHO) as the second reactive groups was synthesized. The title compound was synthesized as disclosed in Biomacromolecules 2013. The aldehyde groups (—CHO) were conjugated to the HA component as disclosed therein, the linker $L_3$ formed was —$NHCH_2$—. The percentage of aldehyde modification in HA was found to be 9% (with respect to the disaccharide units) as determined by $^1H$ NMR spectroscopy. The degree of aldehyde modification was estimated by reacting tert-butyl carbazate with aldehyde modified HA followed by $NaCNBH_3$ reduction and integrating the tert-butyl signal at 1.4 ppm against N-acetyl signal at 2.0 ppm of HA.

Example 4. Preparation of a Hydrogel Composition

The hydrogel composition was prepared using hydrazone crosslinking chemistry. The synthesized HA-DA-CDH (first component of the hydrogel precursor composition) and HA-Ald (second component of the hydrogel precursor composition) components were sterilized with UV for 20 min and dissolved into sterile PBS with a concentration 10 $mgml^{-1}$ (w/v). Sodium hyaluronate (Pharma Grade 150) with $M_w$ of 1200-1900 kDa (Novamatrix) was used as a primary rheological modifier component and was dissolved in sterile 5×PBS with 0.4 M NaCl with a concentration of 10 $mgml^{-1}$ (w/v). The OptiCol™ Human Collagen Type I (3.1 mg/ml) (Cell Guidance Systems Ltd, Cambridge, UK) was introduced into the hydrogel precursor composition as a secondary rheological modifier component for increased biocompatibility and viscoelasticity. Human collagen Type I was neutralized to a pH of 7.4 with 1 M sodium hydroxide (NaOH) in the presence of 10× Dulbecco's Phosphate Buffered Saline (DPBS, Carl Roth, Karlsruhe, Germany). The concentration of the crosslinking components, i.e., the first and second component of the hydrogel precursor composition, in the final hydrogel composition was 5.83 mg/ml. The final hydrogel composition consisted of HA-DA-CDH 29.2% (v/v), HA-Ald 29.2% (v/v), HA 12.5% (v/v), neutralized human collagen type I 18.2% (v/v) and cell culture medium 10.9% (v/v). The mixing of the components was done using a dual syringe system, where two syringes were combined with a female-female luer lock. After thorough mixing, the admixture was placed in a 30 cc Nordson EFD syringe barrel, and the cartridge piston placed in the barrel immediately. The crosslinking components of the admixture were allowed to crosslink and cure at RT for 45 to 60 minutes for forming the printable hydrogel. The crosslinking allows the hydrogel to obtain the optimal consistency and viscosity before using the hydrogel for printing.

Example 5. 3D Printing

The 3D printing was performed with the hydrogel disclosed in the Example 4. Extrusion-based 3D printing with 3D-Bioplotter® Manufacturer Series by Envisiontec (Gladbeck, Germany) was used. After the pre-crosslinking period, a 90 minute biofabrication window for 3D printing was obtained. The barrel with a hydrogel composition was loaded into the low-temperature printhead of the 3D bioprinter. 32 G blunt needle with length of 0.50 inch and inner diameter of 100 μm were used for printing. The printhead temperature was adjusted to 20° C. and the printing was carried out at RT. 3D models in .stl format were created with Perfactory RP Software and the inner parameters including printing patterns were adjusted in Visuals Machine. 80 μm slice interval was used for all printed structures, and needle height was adjusted at 0.07 mm. For 3D printing with the hydrogel comprising cells, i.e., the bioink, a printing pressure of 1.0 bar and printing speed of 6.0 mm/s were used. The 3D printing parameters used for the bioink were otherwise the same as disclosed above.

Example 6. Viscosity and Shear Thinning of the Hydrogel Composition

Figure 2:
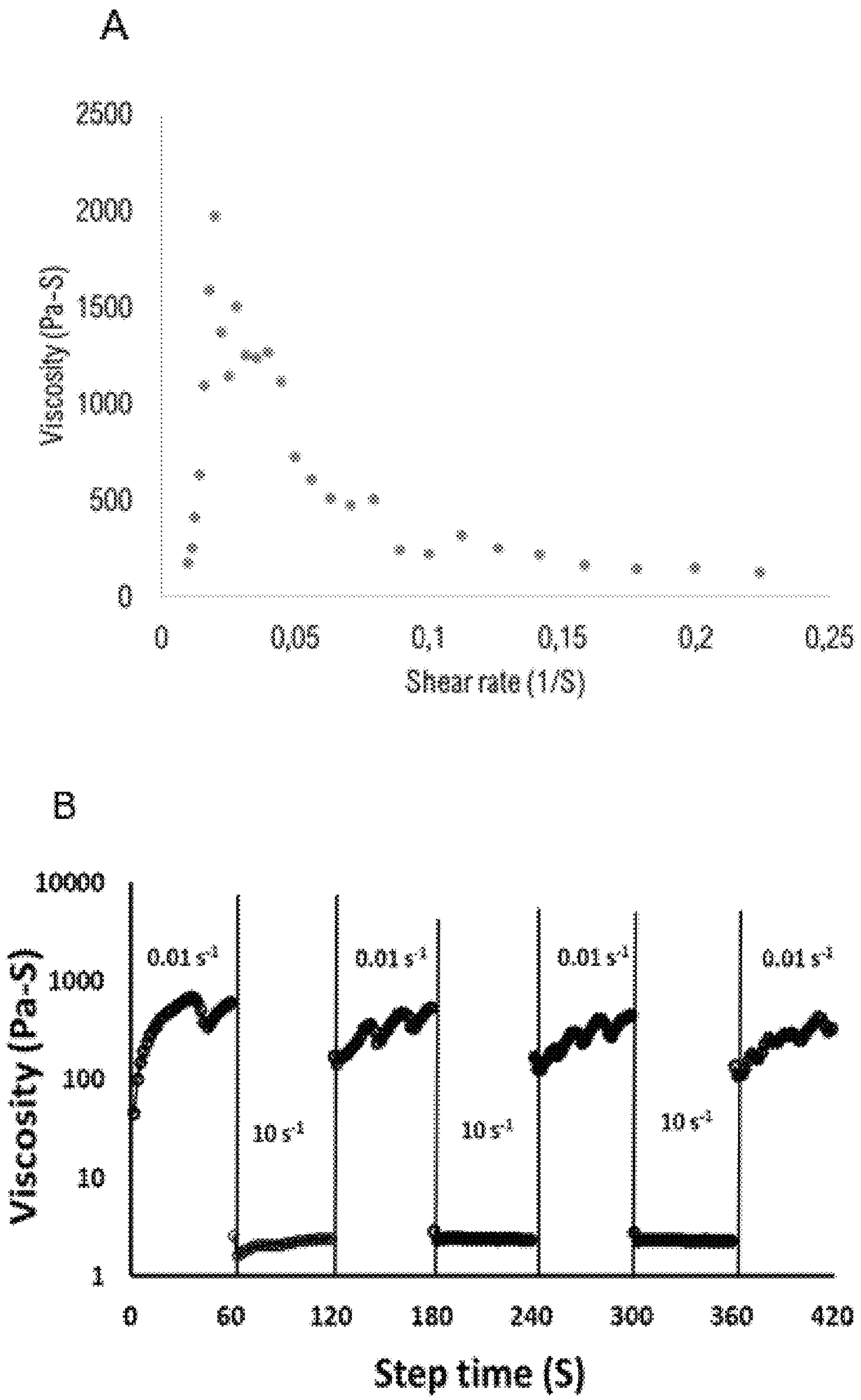
FIG. 2 shows the viscosity A) under continuous flow and B) under periodical flow, indicating the shear thinning behavior of the hydrogel composition according to an example embodiment.
Figure 3:
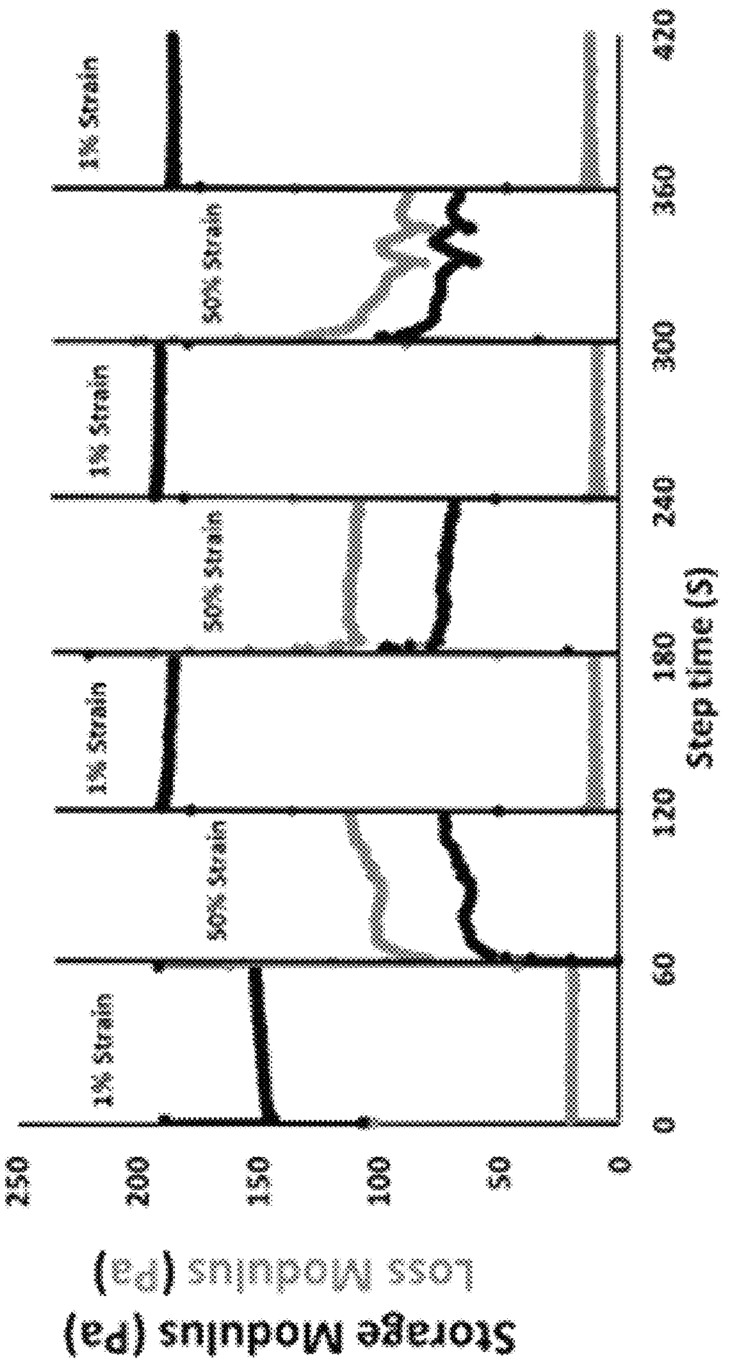
FIG. 3 shows the strain recovery of the hydrogel composition indicated as a storage and loss modulus, according to an example embodiment.

The injectability and shear-thinning property of the hydrogel composition enclosed in the example 4 was determined. The viscosity and flow property of the hydrogel, both under continuous flow (0.01-10 s-1), and under a periodic flow was measured. The shear rates used for periodic flow were 0.01 and 10 s-1 up to seven cycles with 60 secs of holding time for each cycle using 12 mm stainless-steel parallel plate geometry in TA instruments' DHR-II rheometer. The FIG. 2 discloses the viscosity as Pa·s of the hydrogel composition under A) continuous flow and B) periodic flow, indicating the hydrogel composition has excellent injectability and shear-thinning properties. To further evaluate the strain recovery of the crosslinked hydrogel of the Example 4, its storage and loss modulus were measured. The measurements were done under flow alternating between low (1% strain) and high (50% strain) oscillation strain conditions, at 25° C. and 1 Hz oscillation frequency for seven cycles with 60 seconds of holding period in each step using 12 mm diameter stainless steel parallel plate geometry. The results disclosing the storage modulus (Pa) and loss modulus (Pa) of the hydrogel composition in the FIG. 3 indicate the hydrogel composition is shear thinning under strain.

Example 7. 3D Printing with Hydrogel Compositions with and without a Rheological Modifier Component The hydrogel compositions with and without a rheological modifier were tested for 3D printing. The composition disclosed in the Example 4 was used in this experiment as a hydrogel with a rheological modifier. A corresponding hydrogel to the one disclosed in Example 4 was prepared without any rheological modifier. Both hydrogels comprised 5.83 mg/ml of the crosslinking components. Lattice structures with six layers and 2.5 mm distance between strands were printed. Pictures of the printed structures were taking immediately after printing. The hydrogels were allowed to crosslink 1 h in RT before printing and printed thereafter through a 32 G nozzle. Printing parameters of 1.0 bar and 6.0 mm/s were used for both hydrogels.

The printability of these hydrogel compositions, was further compared to a hydrogel composition prepared as disclosed previously by Koivusalo et al. 2019. The hydrogel composition disclosed by Koivusalo et al. 2019 was printed immediately after mixing the crosslinking components as the gelation of the material was very rapid in comparison to the two other hydrogel compositions. Lattice structures with two layers and 2.5 mm distance between lines were used. A larger nozzle of 27 G was used, and a higher pressure of 1.5-2.0 bar was needed for the hydrogel material to flow through the nozzle.

Figure 4:
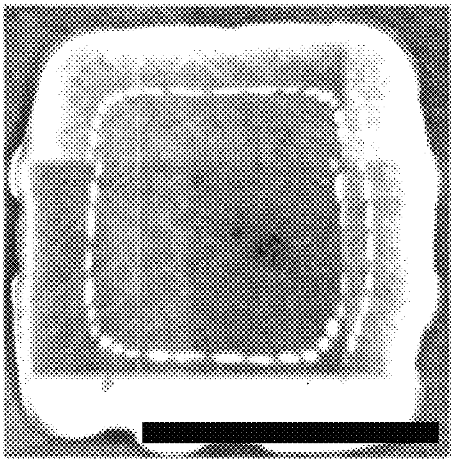
FIG. 4 shows exemplary 3D printed hydrogel lattices produced using hydrogel precursor compositions A) without any rheological modifier, B) according to current invention with sodium hyaluronate and human Collagen Type I as a rheological modifier component, and C) according to the disclosure of Koivusalo et al. 2019, according to an example embodiment, scale bar 10 mm.
Figure 4:
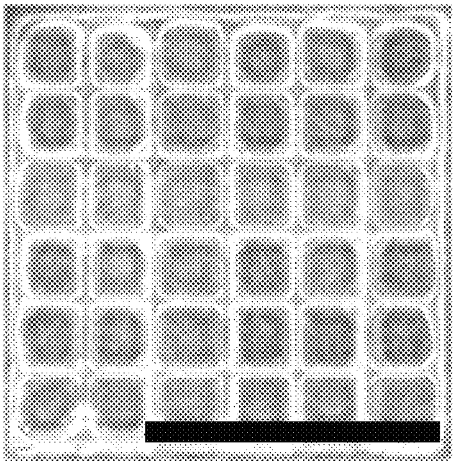
Figure 4:
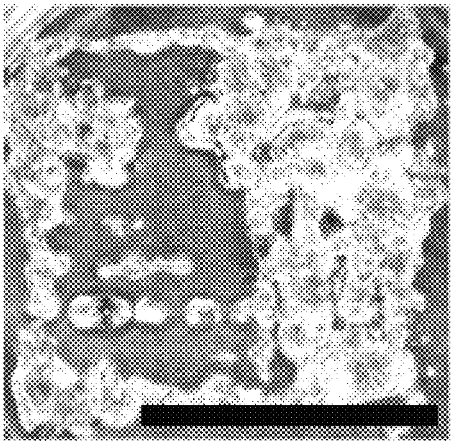

An image indicating the 3D printed hydrogel composition without any rheological modifier component is depicted in in FIG. 4A, an image indicating the 3D printed hydrogel composition with hyaluronic acid and human collagen type I as a rheological modifiers is depicted in FIG. 4B), and an image indicating the 3D printed hydrogel composition of Koivusalo et al. 2019 is depicted in FIG. 4C). These results indicate that a hydrogel comprising the exemplary rheological modifier forms a hydrogel with good printing qualities. These results also indicate that a hydrogel without the rheological modifier does not form a printable filament and it cannot be patterned into specific structures and used for 3D printing as such. Furthermore, the hydrogel composition disclosed by Koivusalo et al 2019 formed lumps and printed unevenly, instead of printing as a continuous filament as the hydrogel composition illustrated in FIG. 4C. This indicates that hydrogel composition described in Koivusalo et al. 2019, comprising a higher concentration of the crosslinking components and no rheological modifier, is not suitable for 3D printing.

Figure 5:
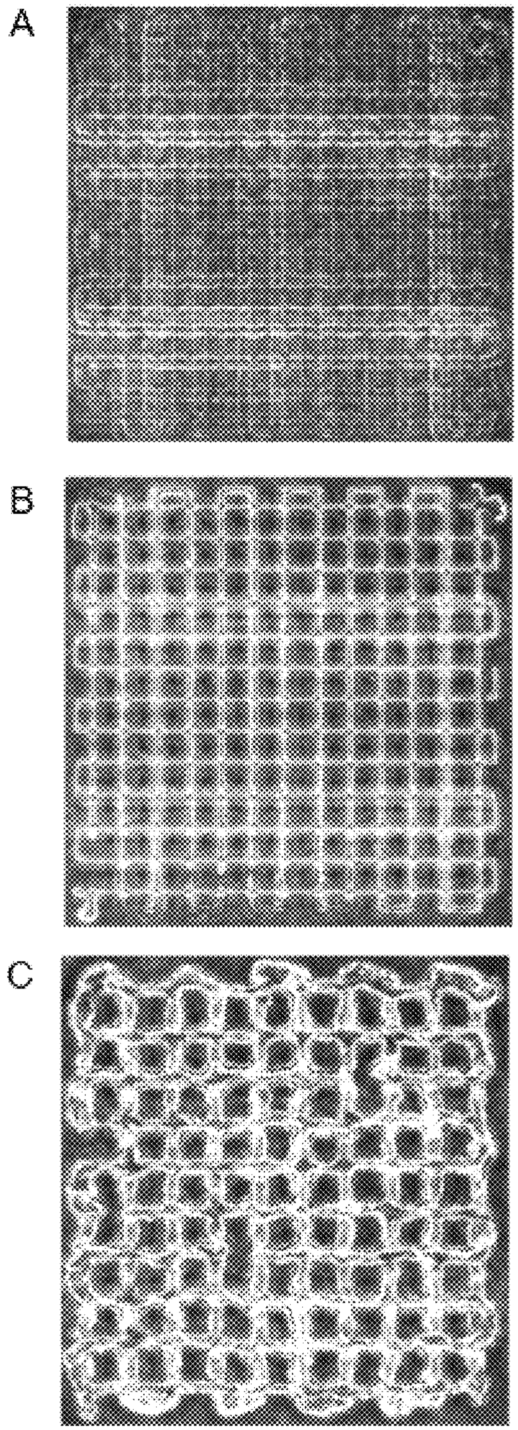
FIG. 5 shows exemplary 3D printed hydrogel lattices produced using hydrogel precursor compositions comprising A) 2.92 mg/ml, B) 8.16 mg/ml, and C) 11.66 mg/ml of the crosslinking components, i.e., the first and the second component of the hydrogel precursor composition, from the final hydrogel composition volume, according to an example embodiment.

Example 8. 3D Printing with Hydrogel Compositions Comprising Different Concentrations of the Crosslinking Components Different concentrations of the crosslinking components in a hydrogel composition were studied for observing effects on the printability of the hydrogels. The same components of the hydrogel precursor composition as in Example 4 were used. Hydrogels with crosslinking component concentrations of 2.92 mg/ml, 8.16 and 11.66 mg/ml were prepared and studied. Lattice structures of 20×20 mm with two layers and line distance of 1.00 mm were printed with 2.92 mg/ml and 8.16 mg/ml crosslinking component concentration hydrogels whereas 15 mm×15 mm lattice with line distance 2.50 mm were used for 11.66 mg/ml crosslinking component concentration hydrogels. 2.92 mg/ml crosslinking component concentration hydrogel was printed using 34 G nozzle with a pressure of 0.2 bar and speed 18 mm/s. For 8.16 mg/ml crosslinking component concentration hydrogel 32 G nozzle was used with printing parameters of pressure of 1.6 bar and speed 5 mm/s. 11.66 mg/ml crosslinking component concentration hydrogels was printed using 27 G nozzle with 1.3 bar and 6 mm/s. The crosslinking period was 1 h for the first two concentrations and 30 min for the latter one. The FIG. 5 presents representative images of hydrogels comprising 2.92 mg/ml (FIG. 5A), 8.16 mg/ml (FIG. 5B), and 11.66 mg/ml (FIG. 5C) of the crosslinking components. The Successful printing with good filament formation and fine-tuned patterning was seen with all three hydrogel compositions, indicating the hydrogel compositions with the studied concentrations of the crosslinking components are suitable to be used in 3D printing.

Figure 6:
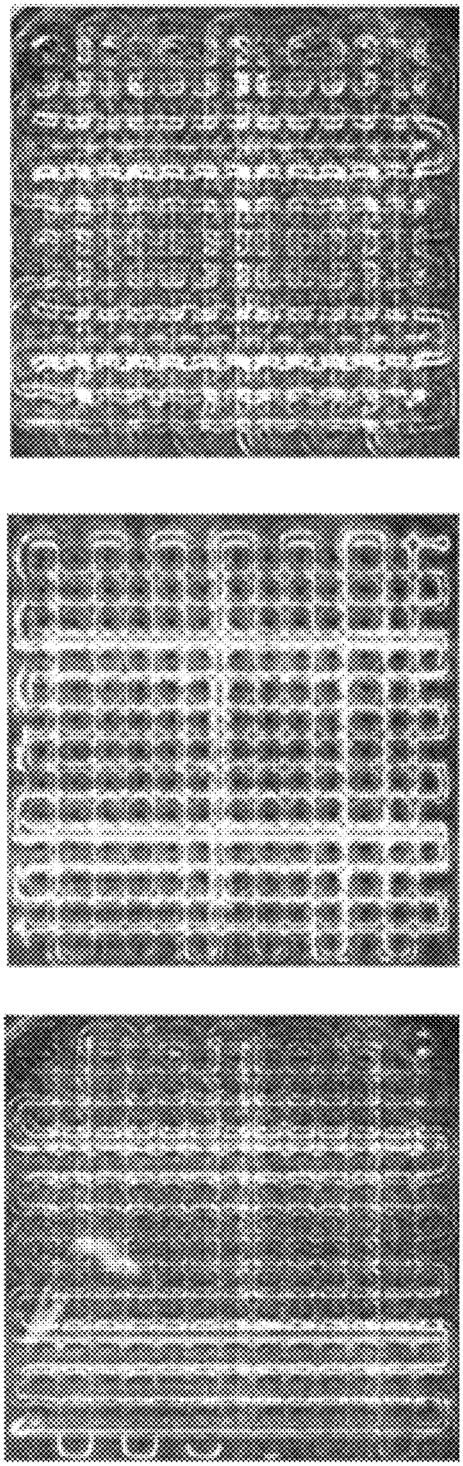
FIG. 6 shows exemplary 3D printed hydrogel lattices produced using hydrogel precursor compositions comprising A) 0.18 mg/ml, B) 0.56 mg/ml, and C) 1.09 mg/ml of collagen type I together with hyaluronic acid (HA) as a rheological modifier component, from the final hydrogel composition volume, according to an example embodiment.

Example 9. 3D Printing with Hydrogel Compositions Comprising Different Concentrations of Collagen Type I as Rheological Modifier The compounding effect of collagen concentration with HA as a rheological modifier component to the printability of the hydrogel was evaluated. The hydrogel composition as disclosed in the Example 4 comprising modified concentrations of collagen type I as the second rheological modifier component were used for the testing. Three hydrogel compositions were prepared, which comprised the same concentration of HA as a rheological modifier, as the composition disclosed in Example 4. All three hydrogel compositions also comprised 5.83 mg/ml of the crosslinking components. The tested neutralized human collagen type I component concentrations in the hydrogels were 0.18 mg/ml, 0.56 mg/ml and 1.09 mg/ml. Printing parameters of 0.9 bar and 6.00 mm/s were used for all investigated hydrogel compositions and all samples were printed into lattice structures of two layers and 20 mm×20 mm with 1.0 mm line distance. 32 G nozzle was used for printing. The exemplary images indicating the 3D printed hydrogel compositions with three different concentrations of human collagen type I as the secondary rheological modifier component are depicted in FIG. 6. The FIG. 6 presents representative images of hydrogels with human collagen type I concentrations of 1 mg/ml (FIG. 6A), 3.1 mg/ml (FIG. 6B), and 6.0 mg/ml (FIG. 6C). An increase in crosslinking and improvement of shape fidelity was observed in hydrogel compositions along with the increase of collagen concentration.

Example 10. 3D Printing with Hydrogel Compositions Comprising Different Concentrations of HA as a Rheological Modifier Component The hydrogel crosslinking component ratios and reagents enclosed in Example 4 were used. Hydrogels with different concentrations of HA as a rheological modifier component were prepared, and their printability was explored. No collagen type I was added as a rheological modifier to these hydrogels. Final HA concentrations of 0.625 mg/ml, 1.25 mg/ml and 3.125 mg/ml in the hydrogels were tested. The hydrogels were printed using 1.3 bar, 8 mm/s, and six layered lattices with 2.50 mm strand distance were 3D printed.

Figure 7:
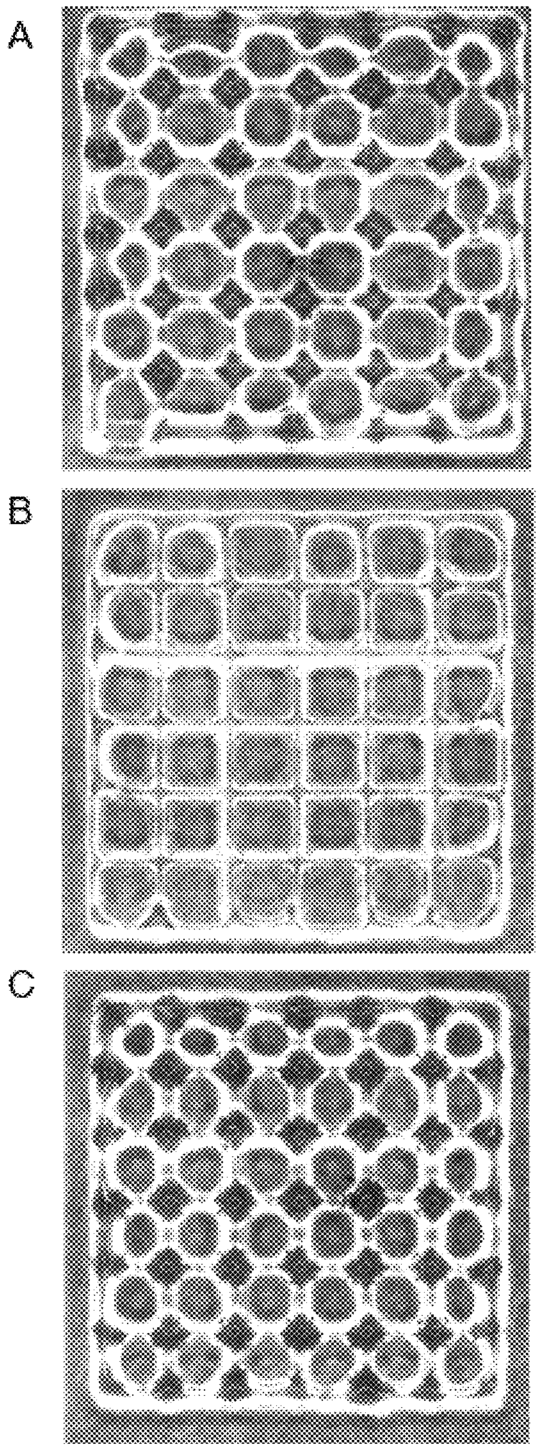
FIG. 7 shows exemplary 3D printed hydrogel lattices, produced using hydrogel precursor compositions comprising A) 0.625 mg/ml, B) 1.25 mg/ml, and C) 3.125 mg/ml of HA as a rheological modifier component from the final hydrogel composition volume, according to an example embodiment.

The results shown in FIG. 7 indicate, the concentration of the HA has an apparent impact on printing quality and shape fidelity of the hydrogel. The concentration of HA at 0.625 mg/ml (FIG. 7A) in the hydrogel appears non-optimal and too low for the multilayered hydrogels to hold their shape. Hydrogel with 3.125 mg/ml (FIG. 7C) of HA concentration is stiffer compared to the other tested concentrations, but filaments spread while printing multilayered 3D structures and therefore this concentration is less optimal. The hydrogel comprising 1.25 mg/ml (FIG. 7B) of HA as a rheological modifier showed the best printability and shape fidelity qualities from the tested concentrations.

Example 11. 3D Printing with Hydrogel Compositions Comprising Various Rheological Modifiers Several different combinations of rheological modifier components in the hydrogel composition were explored and their printability was tested. The hydrogel composition in Example 4 was used with the modification of replacing human collagen type I component with other proteins. Human fibronectin in PBS with final concentration of 0.8 mg/ml in the hydrogel was studied. Moreover, Human recombinant laminin 521 (Biolamina) with final concentration of 0.02 mg/ml in the hydrogel, and human albumin with final concentration of 9.1 mg/ml (Sigma) in the hydrogel were investigated. The hydrogels were allowed to crosslink for 1 h in RT after mixing the components. All prepared hydrogels were printed with 32 G needle with 0.9 bar and 6.0 mm/s.

Figure 8:
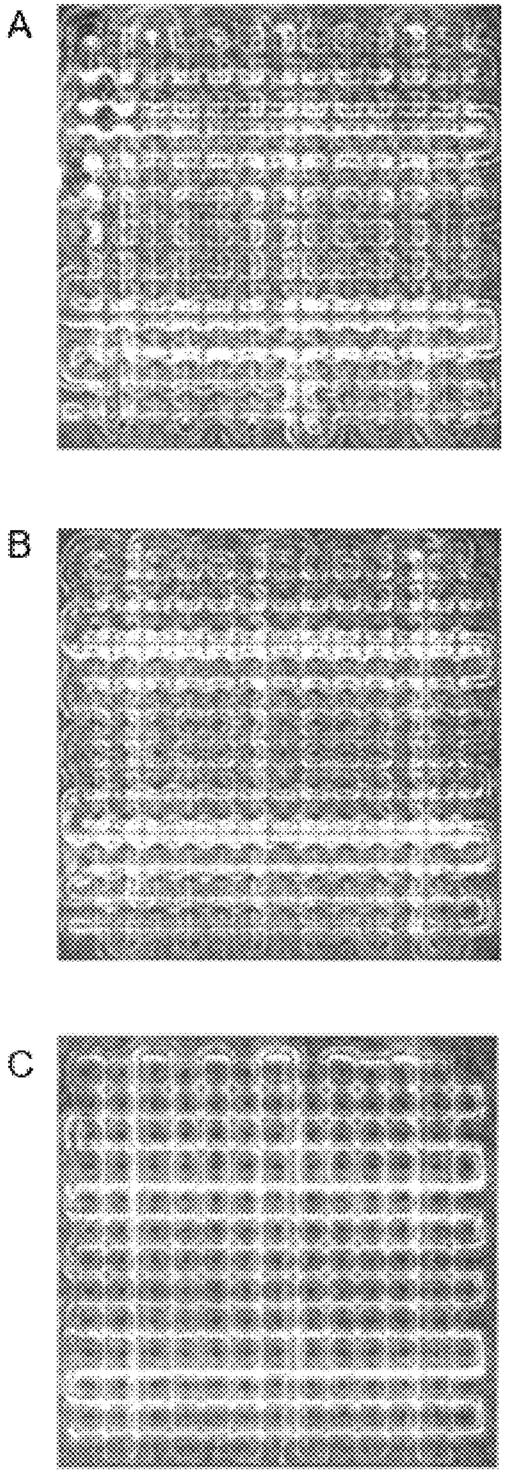
FIG. 8 shows exemplary 3D printed hydrogel lattices, produced using hydrogel precursor compositions with A) laminin, B) albumin or C) fibronectin together with HA as a rheological modifier component, according to an example embodiment.

The FIG. 8 presents representative hydrogel lattices produced using a hydrogel precursor compositions with fibronectin and HA (FIG. 8A), laminin and HA (FIG. 8B), and albumin and HA (FIG. 8C) as a rheological modifier component in the indicated concentrations. Hydrogel compositions with laminin and albumin demonstrated fast crosslinking and very similar behavior to the hydrogel comprising human collagen type I as a rheological modifier. Hydrogel comprising fibronectin was printable, but showed increased filament spreading and reduced printability compared to the other two investigated hydrogel compositions with laminin and albumin. These results indicate that there are several potential combinations of rheological modifiers that can be used in the hydrogel precursor composition, resulting in good crosslinking, and shear thinning properties in the hydrogels.

Example 12. Observing Shape Fidelity of the 3D Printed Hydrogel Composition in a 3D Hydrogel Cylinder Structure For observing the shape fidelity of the 3D printed hydrogel, the hydrogel composition of the Example 4 was used.

Figure 9:
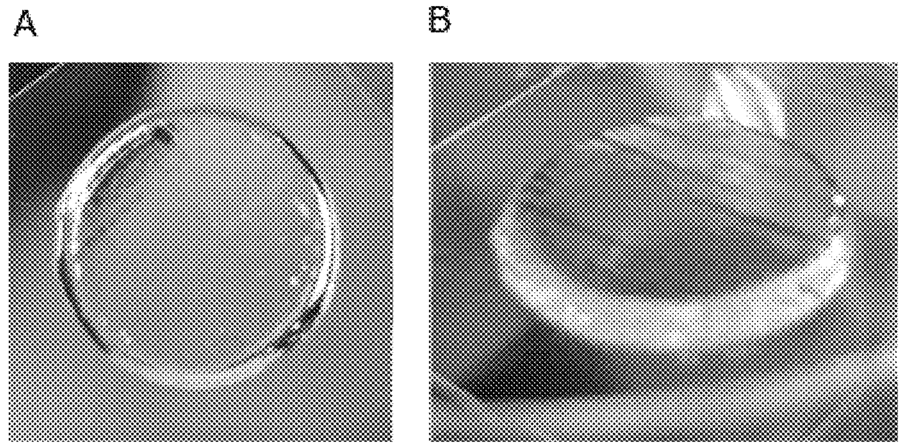
FIG. 9 shows perspective views A) and B) of exemplary printed 3D hydrogel structures, produced using a hydrogel precursor composition according to an example embodiment.

3D cylinders with a diameter of 15 mm and height of 1 mm were printed. The line distance used was 400 μm and the alternative layers were in 90° angle. In the FIG. 9 is shown two perspective exemplary views A and B of the printed 3D structure with 12 printed layers using a 100 μm printing nozzle directly after printing. These results indicate the hydrogel composition prints well layer-by-layer and has a good shape fidelity, when printed in a 3D cylinder shape.

Figure 10:
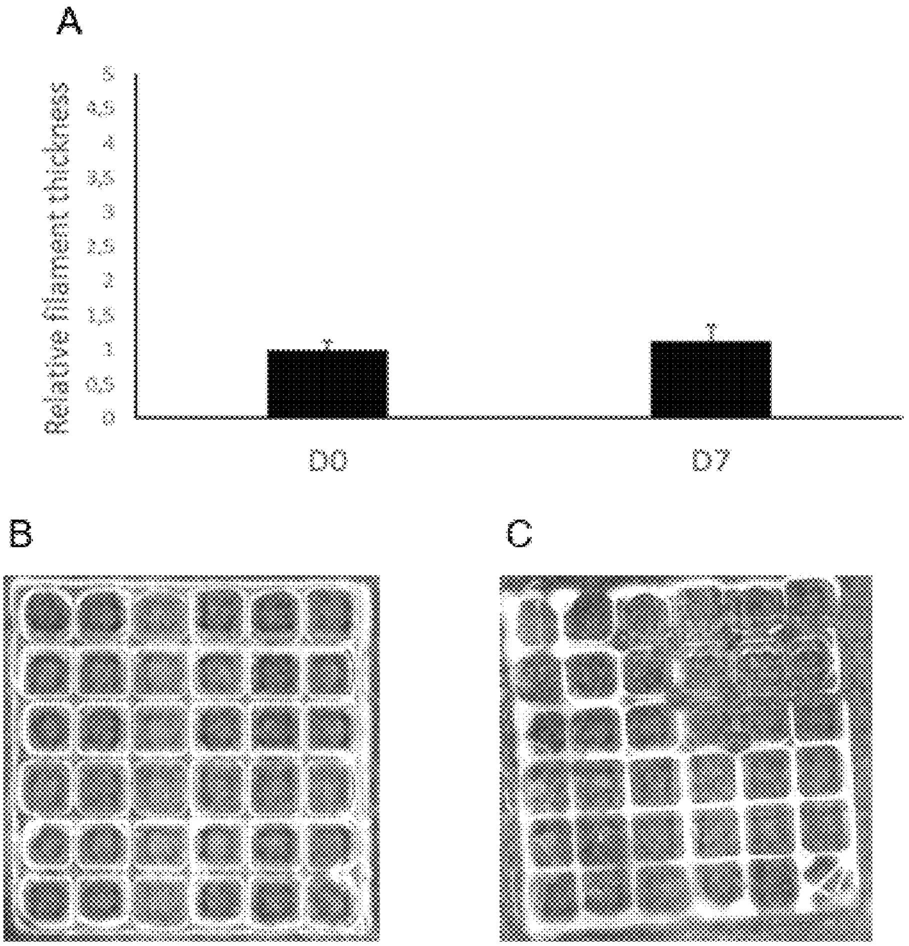
FIG. 10 shows A) a relative filament thickness of an exemplary 3D printed hydrogel lattice as a function of time, DO indicating the relative filament thickness at day 0, and D7 at day 7, and B) an image of the printed hydrogel lattice at day 0 and C) after 7 days, according to an example embodiment.

Example 13. Observing Shape Fidelity of the 3D Printed Hydrogel Composition as a Function of Time For further exploring the shape fidelity of the hydrogel composition, the filament thickness of the hydrogels was measured as a function of time. In this experiment also, the hydrogel composition of the Example 4 was used. The hydrogel was 3D printed in lattices with 6 layers of criss-cross pattern with dimensions of 15 mm×15 mm. Distance of 2.50 mm were used between the printed lines and alternative layers were at 90° angle. The samples were imaged immediately after printing and after 7 days submerged in PBS at +37° C. The thickness of the printed hydrogel filaments was quantified with Image J. The results are presented as relative filament thickness calculated as a ratio of filament thickness at the time the sample was taken, to the filament thickness directly after printing. In the FIG. 10A is shown the calculated relative filament thickness of 3D printed hydrogels as a function of time, D0 indicating the relative filament thickness at day 0, and D7 at day 7. The corresponding images of the printed lattices at day 0 (D0) and at day 7 are demonstrated in FIGS. 10B and 10C, respectively. These results demonstrate that the shape fidelity of the hydrogels does not change significantly over the observed time period. All the pores (36/36) of the printed hydrogel lattice remained open during the 7 day observation period from day 0 (FIG. 10B.) until day 7 (FIG. 10C). Only 12% increase was observed in the relative filament thickness during the culture period of 7 days.

Example 14. Cells and Cell-Culturing

Human adipose-derived stem cells (hASCs) were isolated mechanically and enzymatically from subcutaneous adipose tissue samples as disclosed in art. Thereafter, hASCs were cultured in a medium containing DMEM/F-12 supplemented with 5% human serum (type AB male, HIV tested from BioWest, Nuaillé, France), 1% GlutaMAX™ and 1% penicillin/streptomycin. Human ASCs were passaged upon confluency using TrypLE™ and used for bioprinting at passages 4-5. For bioprinting, hASCs were enzymatically detached with TrypLE™, centrifuged and resuspended in culture medium for counting. Thereafter, hASCs were centrifuged, supernatant was removed and the cells were resuspended in culture medium and mixed with the hydrogel precursor composition in a cell density of $1.1\times10^{6}$ cells $ml^{-1}$, resulting in printable bioink which was used in bioprinting.

In an alternative experimental setup, the hASCs were differentiated into corneal stromal like cells for 7 days in culture before using them in bioprinting. For differentiation hASCs were plated on T75 cell culture flasks with cell density of 7000 $cellscm^{-2}$ in a medium containing Advanced DMEM (Gibco™), 1% GlutaMAX™, 1% penicillin/streptomycin supplemented with 10 ng mL-1 basic fibroblast growth factor (bFGF), 0.1 mM ascorbic acid-2-phosphate and 1 μM retinoic acid. For printing, the predifferentiated cells were prepared as described for hASCs.

Example 15. Biocompatibility of the 3D Printed Hydrogel Composition

The biocompatibility of the hydrogel composition disclosed in the Example 4 was evaluated with hASCs and hASC derived corneal stromal like cells from 3D printed lines and cylinders. The hydrogel composition was prepared and mixed either with hASCs or with hASC derived corneal stromal like cells, thereby resulting in two different bioinks. The bioinks were 3D printed in two layers of parallel lines. The dimension of the printed area was 20 mm×20 mm with line distance of 1.00 mm. 3D cylinders with a diameter of 15 mm and height of 800 μm were for also 3D printed. The line distance used was 400 μm. The alternative layers were in 90° angle. After the 3D printing, the printed lines and cylinders were allowed to form further crosslinks and stabilize at +37° C., with 5% $CO_2$ for 20 minutes before submerging them in cell culture medium or sterile PBS. For higher 3D cylinder sample prints, a stabilization period of 1 h was used before submerging the printed hydrogels in medium or sterile PBS.

The cell viability after printing was determined with PrestoBlue™ Cell Viability Reagent (Invitrogen) after 1, 3 and 7 days of printing. For PrestoBlue® analysis, three samples from each time point from both cell types were washed once with DPBS (Lonza) and PrestoBlue® reagent diluted 1:10 (v/v) in cell culture medium was added to the samples. After a 1 h incubation at 37° C., 100 μL aliquots of PrestoBlue® medium were collected in triplicate from each sample on a 96-well plate and their fluorescence was measured using Viktor 1420 Multilabel Counter (Wallac, Turku, Finland) at excitation and emission wavelengths of 544 nm and 590 nm, respectively.

Figure 11:
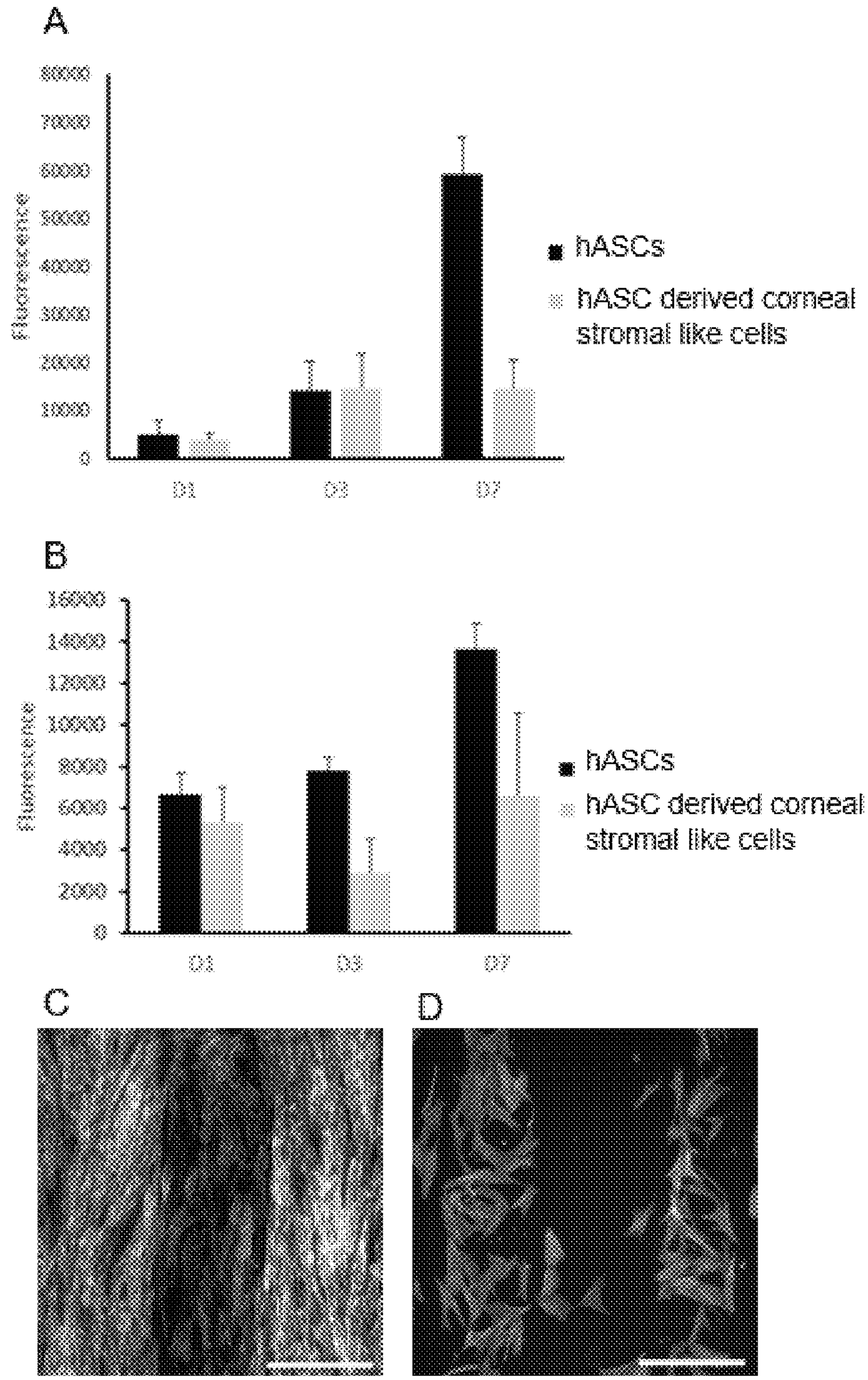
FIG. 11 shows the cell viability of hASCs and hASC derived corneal stromal like cells in exemplary hydrogels at different time points, measured as the emitted fluorescence, indicating the cell viability in A) 3D printed lines, and B) 3D printed structures, and phalloidin staining of 3D printed lines after 7 days of printing in C) hASCs and D) hASC derived corneal stromal like cells according to an example embodiment.

The fluorescence values for the medium samples, are depicted in FIG. 11. D0 indicates the fluorescence at day 0, D3 at day 3, and D7 at day 7. FIG. 11A. indicates the fluorescence in 3D printed double layer bioink lines, and FIG. 11B. indicates the fluorescence in 3D printed non-hollow 3D cylinders with the said cell types. These results indicate the hydrogel used with the cells resulting in printable bioink is biocompatible with multiple cell types, and capable of supporting cell viability post-printing. The increase in fluorescence over time indicates, the hydrogel used with the cells resulting in printable bioink is also capable of promoting cell proliferation with multiple cell types post printing. The cell morphology of both printed cell types was evaluated with IF staining of the actin filaments of cells after D7. In brief, the printed lines we fixed with 4% PFA for 30 minutes, washed and permeabilized with 0.1% Triton-X-100 in PBS for 15 minutes in RT, and thereafter blocked with 5% BSA in PBS for 1 h in RT. Phalloidin (Sigma) was diluted in 5% BSA-PBS solution with the ratio of 1:100 and incubated 1 h in RT. The samples were washed three times with PBS and immunofluorescence images were taken with Olympus IX 51 fluorescence microscope. The IF-images of hASCs and hASC derived corneal stromal like cells are depicted in FIGS. 11C and D, respectively (scale bar 500 μm).

Both cell types had elongated cell morphology, which indicated good biocompatibility and cell and tissue maturation in the bioink.

Figure 12:
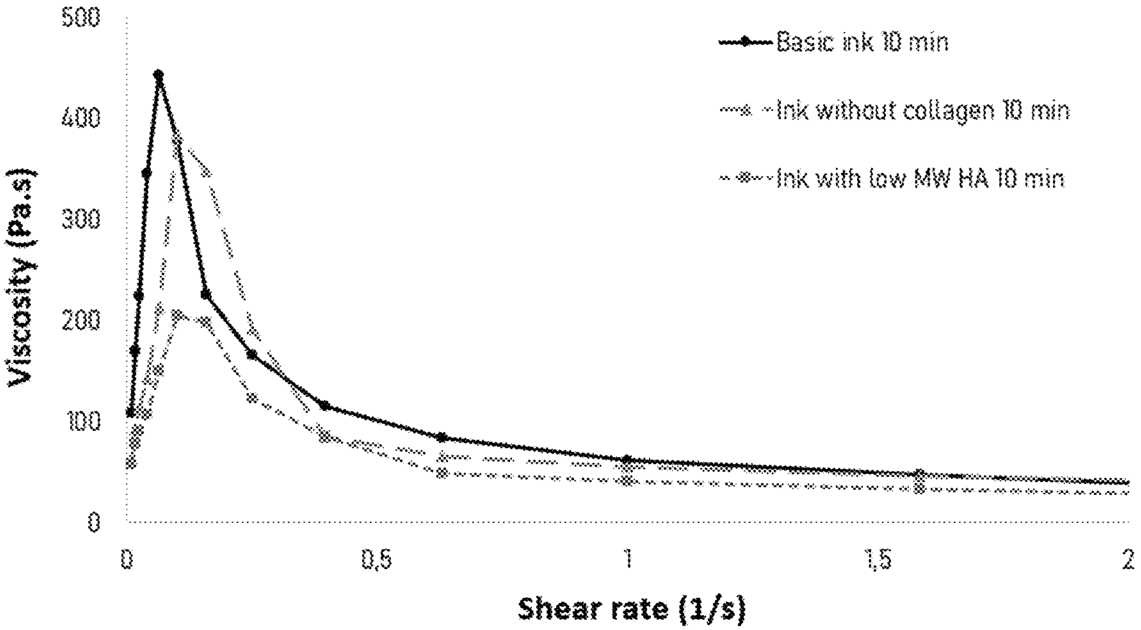
FIG. 12 shows viscosity after 10 minutes of crosslinking for a bioink with high molecular weight HA and Col I as rheological modifier (basic ink), same ink without the Col I and a bioink with low Mw HA as a rheological modifier.
Figure 13:
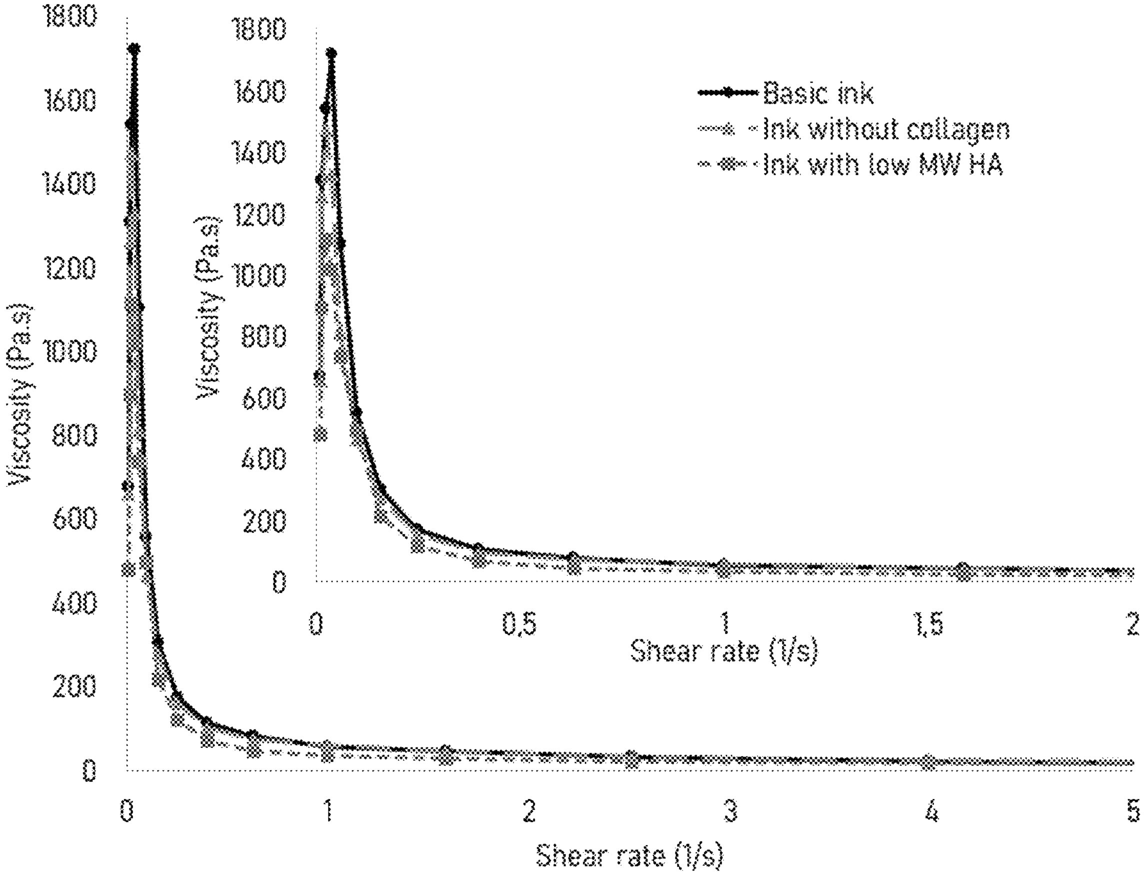
FIG. 13 shows viscosity after 1 hour of crosslinking for a bioink with high molecular weight HA and Col I as rheological modifier (basic ink), same ink without the Col I and a bioink with low Mw HA as a rheological modifier.

Example 16. Observing the Effect of the Mw of the Rheological Modifiers on the Hydrogel Properties The effect of the composition and Mw of the rheological modifiers for hydrogel composition disclosed in Example 4 was evaluated. Hydrogel composition with high Mw HA (Mw=1200-1900 kDa) and Human Collagen type I as rheological components disclosed in Example 4 was used as a control (basic bioink). Similar hydrogel composition as disclosed in Example 4 without the Human Collagen type I was also explored (Bioink without the collagen). Finally, the rheological components of the hydrogel disclosed in Example 4 was replaced with low Mw HA (Mw 100-300 kDa). The injectability and shear-thinning property of these hydrogel compositions was determined under continuous flow (0.01-10 $s^{-1}$) with in TA instruments' DHR-II rheometer after 10 min and 1 h of crosslinking in RT. The basic bioink composition showed highest viscosity after 10 minutes (FIG. 12). and 1 h (FIG. 13) of crosslinking. The viscosity of basic bioink was higher compared to the similar hydrogel composition without the collagen. The hydrogel composition with low Mw HA showed the lowest viscosity values in both time points. These results indicate that the Mw of used HA as a rheological modifier has a significant effect on the viscosity and printability of the developed hydrogel. Moreover, the compound effect of using both high Mw HA and Human Collagen Type I as rheological modifiers is beneficial for the printability of the hydrogel composition.

Example 17. The Effect of Human Collagen Type I on Hydrogel Properties

Figure 14:
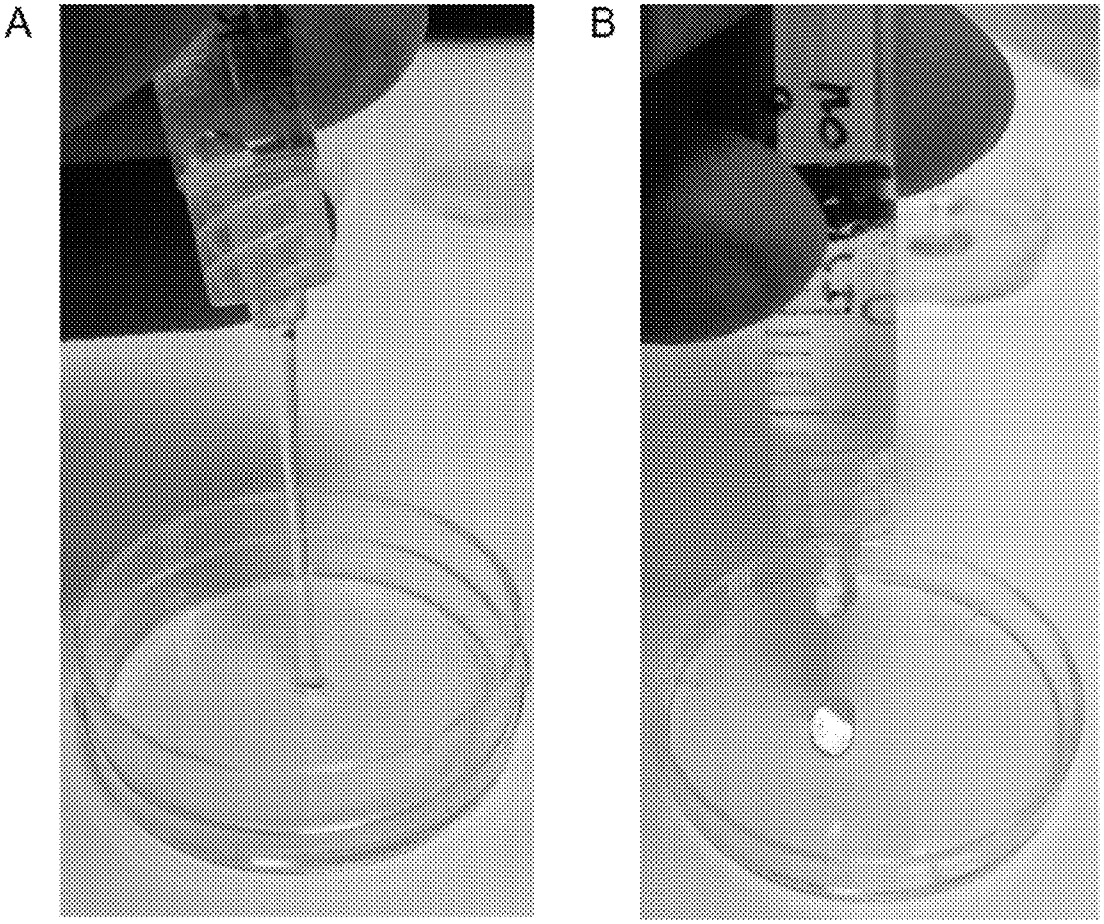
FIG. 14 A) shows that combination of Col I and high molecular weight HA as rheological modifier results in stretchable bioink and sticky material and B) shows that without Col I, the same bioink is not stretchable and breaks while pulling.
Figure 15:
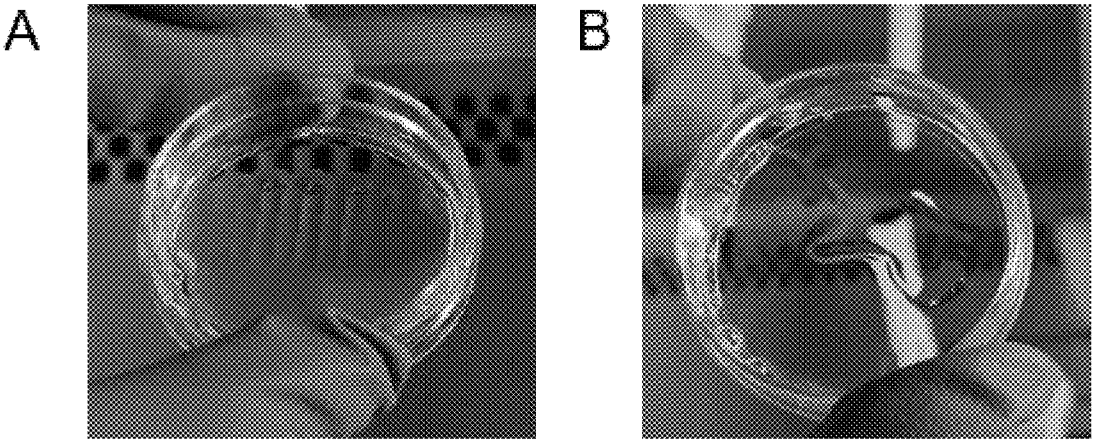
FIG. 15 A) shows that combination of high molecular weight HA and Col I as rheological modifiers results in sticky bioink that maintains it printed form in culture and does not detach from the bottom of dish in culture; B) shows that without Col I, the same bioink detaches from the dish in culture and loses the printed structure.

The effect of the human collagen type I on the hydrogel composition disclosed in Example 4 was evaluated. For this, the hydrogel composition disclosed in Example 4 was compared to similar hydrogel composition without the human collagen type I component. Both hydrogels were allowed to crosslink for 1 h in RT. The elasticity and filament formation were then evaluated by slightly extruding hydrogels from syringes and pulling the hydrogel. The hydrogel composition with Human collagen type I showed excellent filament formation and elasticity (FIG. 14A). The hydrogel with collagen stretched into long fibers. The hydrogel with collagen was sticky and did not detach from the substrate after stretching multiple times. The hydrogel without the collagen type I failed to formed fibers and showed poor elasticity (FIG. 14B). Both hydrogels were 3D bio printed into two layers of parallel lines as enclosed in Example 15. The printed lines were placed in cell culture medium and inspected for adhesion to substrate and shape fidelity. The hydrogel composition with collagen I stayed attached to the printing substrate and maintained the printed line form (FIG. 15A). In contrast, the hydrogel composition without the collagen type I detached from the printing substrate in cell culture medium and lost the printed organized line pattern (FIG. 15B). These results indicate that the combination of Human collagen Type I and high Mw HA result in s unique hydrogel composition with excellent printability, elasticity, stickiness and filament formation.

Example 18. The Effect Mw on the HA-DA-CDH Synthesis and Hydrogel Composition

Figure 16:
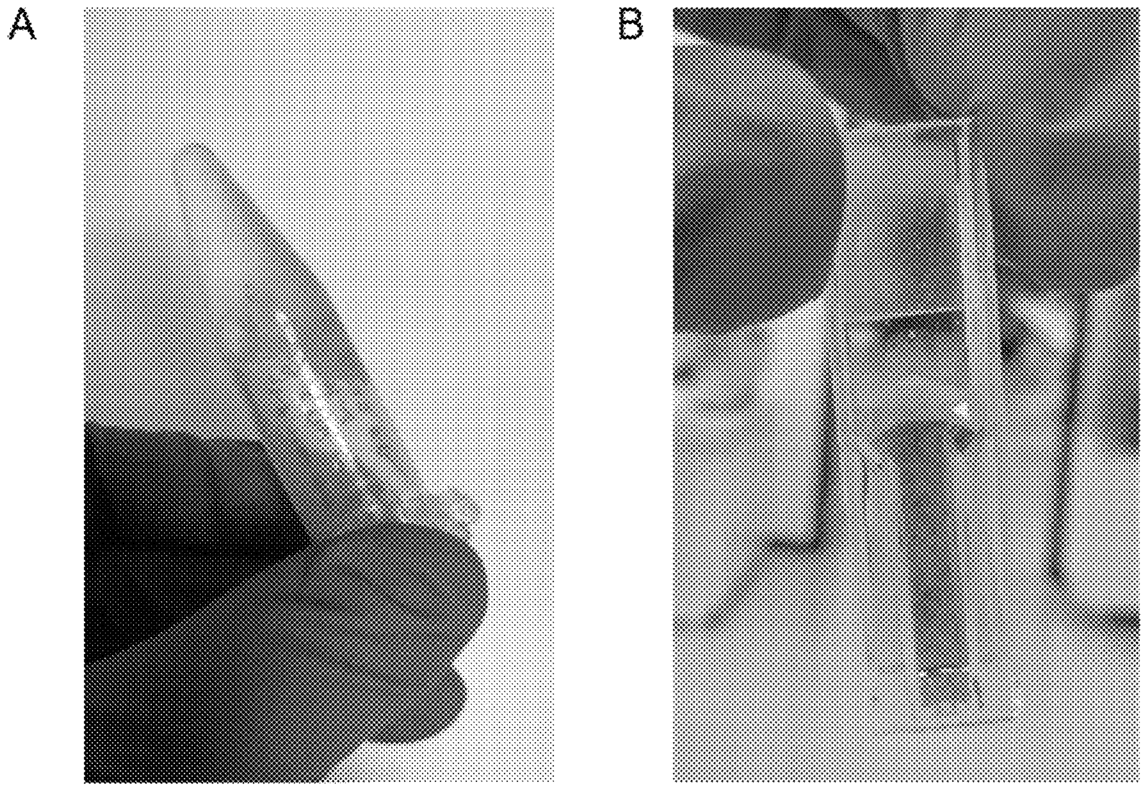
FIG. 16 A) shows that synthesis of high molecular weight HA results in components that do not dissolve and cannot be used for printing; B) shows that synthesized high molecular weight HA-DA-CDH cannot be analyzed and characterized as the components do not dissolve in the reagent solution.

HA-DA-CDH was synthesized as described in Example 2 with the modification using high Mw HA (Mw=1200-1900 kDA). The synthesized HA-DA-CDH was explored for preparing hydrogel composition enclosed in Example 4. For this, the HA-DA-CDH was dissolved in 1×PBS. The solution was incubated in +37° C. for 5 hours under continuous shaking. The HA-DA-CDH did not dissolve into 1×PBS into concentration of 10 mg/ml (FIG. 16A). To determine the synthesis degree of the prepared HA-DA-CDH component, TNBS assay was used. The synthesized component did not dissolve into reagent solvent (FIG. 16B) and the quantification with TNBS assay could not have been done. These results indicate that the high Mw HA is not suitable for the synthesis of HA-DA-CDH to prepare the hydrogel composition.

The foregoing description has provided by way of non-limiting examples of particular implementations and embodiments a full and informative description of the best mode presently contemplated by the inventors for carrying out the invention. It is however clear to a person skilled in the art that the invention is not restricted to details of the embodiments presented in the foregoing, but that it can be implemented in other embodiments using equivalent means or in different combinations of embodiments without deviating from the characteristics of the invention.

Furthermore, some of the features of the afore-disclosed example embodiments may be used to advantage without the corresponding use of other features. Consequently, any appropriate combination of the embodiments and the aspects may be formed. Any combination of aspects or embodiments as disclosed herein may also be made without at least one non-essential feature disclosed in an aspect or embodiment.

Different non-binding example aspects and embodiments have been illustrated in the foregoing. The embodiments in the foregoing are used merely to explain selected aspects or steps that may be utilized in different implementations. Some embodiments may be presented only with reference to certain example aspects. It should be appreciated that corresponding embodiments may apply to other example aspects as well. The appended claims define the scope of protection. Any method, process, use, product or apparatus disclosed in the description or drawing, and which is not covered by a claim, is provided as an example which is not to be understood as an embodiment of the claimed invention, but which is useful for understanding the claimed invention.

REFERENCES

Biomacromolecules 2013, 14, 7, 2427-2432, Publication Date: May 30, 2013, https://doi.org/10.1021/bm400612h Koivusalo L. et al. Biomaterials 2019, 225, Publication Date: Sep. 23, 2019, https://doi.org/10.1016/j.biomaterials.2019.119516

The invention claimed is:

1. A hydrogel precursor composition for bioink comprising:

i. a first component comprising a hyaluronic acid (HA) component conjugated to a. plurality of carbohydrazide groups (—$CONHNH_2$) wherein the carbohydrazide groups are conjugated to 5-20% of disaccharide repeat units of the HA component of the first component via linker L1 wherein said linker is —NHNH—, and b. plurality of catechol groups wherein the catechol group are conjugated to 1-20% of disaccharide repeat units of the HA component of the first component via a linker L2, wherein said linker is —$NH(CH_2)_2$—;

ii. a second component comprising a hyaluronic acid (HA) component conjugated to plurality of aldehyde groups, wherein the aldehyde groups are conjugated to 5-50% of the disaccharide repeat units of the HA component of the second component via a linker L3, wherein said linker is —$NHCH_2$ wherein molecular weight of the HA component of first component and the HA component of the second component is 100-300 kDa, and wherein the aldehyde groups are configured to form crosslinks with the carbohydrazide groups; and iii. a rheological modifier component;

wherein the rheological modifier component comprises hyaluronic acid with a molecular weight of 1200 kDa-1900 kDa, and collagen with molecular weight of 250-300 kDa, and wherein the rheological modifier component comprises 2-50 wt-% from the total weight of the hydrogel precursor composition.

2. The hydrogel precursor composition of claim 1, wherein, the rheological modifier component of the hydrogel precursor composition further comprises alginate, chitosan, nanocellulose, polyethylene glycol, poloxamer, polyvinyl alcohol, an extracellular matrix protein, albumin, or mixtures thereof.

3. The hydrogel precursor composition of claim 1, wherein the rheological modifier component of the hydrogel precursor composition further comprises human fibronectin with a molecular weight of 440-530 kDa.

4. The hydrogel precursor composition of claim 1, wherein the rheological modifier component of the hydrogel precursor composition further comprises laminin, with a molecular weight of 400-900 kDa.

5. The hydrogel precursor component according to claim 1, wherein the rheological modifier component further comprises one or more extracellular matrix proteins.

6. A bioink obtainable by mixing the hydrogel precursor composition according to claim 1, with a fluid comprising cells.

7. A method for 3D printing a bioink, the method comprising:

a) producing the bioink by mixing the hydrogel precursor composition according to claim 1 with a fluid comprising cells;

b) allowing the first component of the hydrogel precursor composition to crosslink with the second component of the hydrogel precursor composition in said fluid, and c) 3D printing the bioink when the viscosity of the bioink is 200-2000 Pa·s.

* * * * *